US012588864B2

(12) United States Patent
Mikhail et al.

(10) Patent No.: US 12,588,864 B2
(45) Date of Patent: Mar. 31, 2026

(54) SENSORS IMPLANTABLE INTO A PATIENT'S BODY, SYSTEMS, AND METHODS OF USING THE SAME

(71) Applicant: DePuy Synthes Products, Inc., Raynham, MA (US)

(72) Inventors: George Mikhail, Downingtown, PA (US); Filip Leszko, West Chester, PA (US); Glen Pierson, Glenmoore, PA (US); Brett Ivan Wakley, Boston, MA (US); Arun Venkatasubramanian, Singapore (SG); Rostislav Lemdiasov, Newton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 95 days.

(21) Appl. No.: 16/056,623

(22) Filed: Aug. 7, 2018

(65) Prior Publication Data

US 2019/0038214 A1 Feb. 7, 2019

Related U.S. Application Data

(60) Provisional application No. 62/541,924, filed on Aug. 7, 2017.

(51) Int. Cl.
*A61B 5/00* (2006.01)
*A61B 5/11* (2006.01)
(Continued)

(52) U.S. Cl.
CPC .......... *A61B 5/4538* (2013.01); *A61B 5/0004* (2013.01); *A61B 5/0031* (2013.01);
(Continued)

(58) Field of Classification Search
CPC .......... A61B 5/4538; A61B 5/11; A61B 5/45; A61B 5/0031; A61B 5/0004;
(Continued)

(56) References Cited

U.S. PATENT DOCUMENTS

| 4,145,921 A | 3/1979 | Blackwelder |
| 4,281,538 A | 8/1981 | Dudek |

(Continued)

FOREIGN PATENT DOCUMENTS

| CN | 1123187 A | 5/1996 |
| CN | 101524298 A | 9/2009 |

(Continued)

OTHER PUBLICATIONS

Anonymous: "PICOSTRAIN Measurement Principle | PMT", Jun. 14, 2016 (2016-06-14), XP055514840, Retrieved from the Internet: URL:https://web.archive.org/web/20160614121258/http://www.pmt-fl.com:80/picostrain/picostrain-measuring-method-overview.php [retrieved on Feb. 4, 2019].

*Primary Examiner* — Tse W Chen
*Assistant Examiner* — Joseph A Tombers
(74) *Attorney, Agent, or Firm* — BakerHostetler

(57) ABSTRACT

In one example, a sensor is configured to be implanted into a patient's body. The sensor has at least one sensing element, a measurement device in communication with the at least one sensing element, and an internal wireless communicator in communication with the measurement device. The at least one sensing element includes a resistor, and the measurement device includes a capacitor. The measurement device measures a discharge time of the capacitor through the resistor so as to generate a measurement value that is proportional to a value of an anatomical property of the anatomical body, such as strain, that is observed by the sensor. The internal wireless communicator wirelessly com- (Continued)

municates the measurement value through skin of the patient to an external wireless communicator situated outside of the patient's body.

19 Claims, 9 Drawing Sheets

(51) Int. Cl.

| | |
|---|---|
| *G01R 19/255* | (2006.01) |
| *G01R 27/02* | (2006.01) |
| *H01Q 1/52* | (2006.01) |
| *H01Q 7/00* | (2006.01) |

(52) U.S. Cl.
CPC .................. *A61B 5/11* (2013.01); *A61B 5/45* (2013.01); *A61B 5/4504* (2013.01); *A61B 5/6878* (2013.01); *G01R 27/02* (2013.01); *H01Q 1/526* (2013.01); *H01Q 7/00* (2013.01); *A61B 2562/0261* (2013.01); *A61B 2562/043* (2013.01); *A61B 2562/182* (2013.01); *G01R 19/255* (2013.01)

(58) Field of Classification Search
CPC ................ A61B 5/6878; A61B 5/4504; A61B 2562/182; A61B 2562/0261; A61B 2562/043; G01R 27/02; G01R 19/255; H01Q 7/00; H01Q 1/526
See application file for complete search history.

(56) References Cited

U.S. PATENT DOCUMENTS

| | | | |
|---|---|---|---|
| 4,626,041 | A | 12/1986 | Harbour |
| 5,144,309 | A * | 9/1992 | Adams .................... H03M 1/50 341/118 |
| 5,535,752 | A | 7/1996 | Halperin et al. |
| 5,873,843 | A | 2/1999 | Draper |
| 5,962,792 | A | 10/1999 | Kimerer, Jr. |
| 6,018,298 | A | 1/2000 | Endo et al. |
| 6,034,296 | A | 3/2000 | Elvin et al. |
| 6,143,035 | A | 11/2000 | McDowell |
| 6,447,448 | B1 | 9/2002 | Ishikawa et al. |
| 6,456,076 | B1 | 9/2002 | Joseph |
| 6,610,096 | B2 | 8/2003 | MacDonald |
| 6,706,005 | B2 | 3/2004 | Roy et al. |
| 6,796,187 | B2 | 9/2004 | Srinivasan et al. |
| 6,962,088 | B2 | 11/2005 | Masashi |
| 7,182,736 | B2 | 2/2007 | Roy et al. |
| 7,245,117 | B1 | 7/2007 | Joy et al. |
| 7,256,695 | B2 | 8/2007 | Hamel et al. |
| 7,302,858 | B2 | 12/2007 | Walsh et al. |
| 7,357,037 | B2 | 4/2008 | Hinat et al. |
| 7,432,723 | B2 | 10/2008 | Ellis et al. |
| 7,439,723 | B2 | 10/2008 | Allen et al. |
| 7,466,120 | B2 | 12/2008 | Miller et al. |
| 7,478,108 | B2 | 1/2009 | Townsend et al. |
| 7,491,179 | B2 | 2/2009 | Roy et al. |
| 7,498,799 | B2 | 3/2009 | Allen et al. |
| 7,509,870 | B2 | 3/2009 | Aebersold et al. |
| 7,550,978 | B2 | 6/2009 | Joy et al. |
| 7,679,355 | B2 | 3/2010 | Allen et al. |
| 7,786,867 | B2 | 8/2010 | Hamel et al. |
| 7,839,153 | B2 | 11/2010 | Joy et al. |
| 7,854,174 | B2 | 12/2010 | Aebersold et al. |
| 7,878,988 | B2 | 2/2011 | Bush et al. |
| 7,932,732 | B2 | 4/2011 | Ellis et al. |
| 7,936,174 | B2 | 5/2011 | Ellis et al. |
| 7,970,734 | B2 | 6/2011 | Townsend et al. |
| 7,973,540 | B2 | 7/2011 | Kroh et al. |
| 8,026,729 | B2 | 9/2011 | Kroh et al. |
| 8,032,486 | B2 | 10/2011 | Townsend et al. |
| 8,043,290 | B2 | 10/2011 | Harrison et al. |
| 8,066,650 | B2 | 11/2011 | Lee et al. |
| 8,070,695 | B2 | 12/2011 | Gupta et al. |
| 8,083,741 | B2 | 12/2011 | Morgan et al. |
| 8,237,451 | B2 | 8/2012 | Joy et al. |
| 8,264,240 | B2 | 9/2012 | Park et al. |
| 8,278,941 | B2 | 10/2012 | Kroh et al. |
| 8,343,153 | B2 | 1/2013 | Duda et al. |
| 8,486,070 | B2 | 7/2013 | Morgan et al. |
| 8,516,884 | B2 | 8/2013 | Stein et al. |
| 8,529,474 | B2 | 9/2013 | Gupta et al. |
| 8,622,936 | B2 | 1/2014 | Schenberger et al. |
| 8,687,865 | B2 | 4/2014 | Wilson et al. |
| 8,721,570 | B2 | 5/2014 | Gupta et al. |
| 8,721,643 | B2 | 5/2014 | Morgan et al. |
| 8,896,324 | B2 | 11/2014 | Kroh et al. |
| 8,926,674 | B2 | 1/2015 | Wolter et al. |
| 9,041,416 | B2 | 5/2015 | Park et al. |
| 9,060,743 | B2 | 6/2015 | Munro et al. |
| 9,326,728 | B2 | 5/2016 | Demir et al. |
| 9,510,785 | B2 | 12/2016 | Munro et al. |
| 2002/0068930 | A1 | 6/2002 | Tasto et al. |
| 2003/0030451 | A1 * | 2/2003 | Braun .................... G01R 27/02 324/678 |
| 2004/0011137 | A1 | 1/2004 | Hinat et al. |
| 2006/0052782 | A1 * | 3/2006 | Morgan ............. A61B 5/14539 606/60 |
| 2006/0224088 | A1 | 10/2006 | Roche |
| 2008/0300597 | A1 | 12/2008 | Morgan et al. |
| 2009/0082833 | A1 * | 3/2009 | Wosmek ................ H01Q 1/526 607/60 |
| 2009/0228063 | A1 | 9/2009 | Dlugos, Jr. et al. |
| 2010/0094306 | A1 | 4/2010 | Chang et al. |
| 2011/0098603 | A1 | 4/2011 | Deirmengian et al. |
| 2011/0098966 | A1 | 4/2011 | Suzuki |
| 2011/0152725 | A1 * | 6/2011 | Demir .................... A61B 5/103 600/587 |
| 2011/0307060 | A1 | 12/2011 | Lozier et al. |
| 2011/0319787 | A1 | 12/2011 | Lamoise et al. |
| 2012/0190989 | A1 * | 7/2012 | Kaiser .................... A61B 7/006 600/476 |
| 2012/0191989 | A1 | 7/2012 | Michishita |
| 2012/0253345 | A1 | 10/2012 | Wixted |
| 2012/0277746 | A1 * | 11/2012 | Morgan ................ A61B 17/72 606/62 |
| 2013/0190654 | A1 * | 7/2013 | Deirmengian ......... A61B 17/80 600/587 |
| 2013/0201049 | A1 | 8/2013 | Sugimoto |
| 2014/0084943 | A1 | 3/2014 | Kroh et al. |
| 2014/0176384 | A1 * | 6/2014 | Yosui ....................... H01Q 7/08 343/788 |
| 2014/0378783 | A1 | 12/2014 | Ledet et al. |
| 2015/0083796 | A1 | 3/2015 | Kyung et al. |
| 2015/0255995 | A1 | 9/2015 | Park |
| 2015/0257799 | A1 | 9/2015 | Janna et al. |
| 2015/0289796 | A1 | 10/2015 | Deirmengian et al. |
| 2015/0327896 | A1 | 11/2015 | Bottlang et al. |
| 2016/0128573 | A1 | 5/2016 | Wilder et al. |
| 2016/0198981 | A1 | 7/2016 | Demir et al. |
| 2016/0213319 | A1 | 7/2016 | Ogrodnik et al. |
| 2016/0322849 | A1 * | 11/2016 | Yeh ......................... H02J 50/70 |
| 2016/0354174 | A1 | 12/2016 | Demir |
| 2017/0236638 | A1 * | 8/2017 | Mayo ....................... H01Q 7/00 307/104 |
| 2018/0055444 | A1 | 3/2018 | Windolf |
| 2018/0103899 | A1 * | 4/2018 | Cahan .................. G01L 5/1627 |
| 2018/0310824 | A1 * | 11/2018 | Windolf .............. A61B 5/0031 |
| 2019/0130054 | A1 | 5/2019 | Benker et al. |

FOREIGN PATENT DOCUMENTS

| | | |
|---|---|---|
| CN | 102084230 A | 6/2011 |
| CN | 102292024 A | 12/2011 |
| CN | 103096792 A | 5/2013 |
| CN | 103637840 A | 3/2014 |
| CN | 104066394 A | 9/2014 |
| CN | 105246427 A | 1/2016 |
| CN | 106725471 A | 5/2017 |
| EP | 1251357 A1 | 10/2002 |
| JP | 10-198873 A | 7/1998 |

(56)          References Cited

FOREIGN PATENT DOCUMENTS

| JP | 2009-505751 | A | 2/2009 |
| JP | 2013-056173 | A | 3/2013 |
| RU | 2442964 | C1 | 2/2012 |
| WO | 2005/067796 | A1 | 7/2005 |
| WO | 2007/025191 | A1 | 3/2007 |
| WO | 2015/036784 | A1 | 3/2015 |
| WO | 2016/122148 | A1 | 8/2016 |
| WO | 2016/169578 | A1 | 10/2016 |
| WO | 2016/172806 | A1 | 11/2016 |

* cited by examiner

SENSORS IMPLANTABLE INTO A PATIENT'S BODY, SYSTEMS, AND METHODS OF USING THE SAME

CROSS-REFERENCE TO RELATED APPLICATIONS

This application claims the benefit of U.S. Provisional Application Ser. No. 62/541,924, filed Aug. 7, 2017, the disclosure of which is hereby incorporated by reference as if set forth in its entirety herein.

TECHNICAL FIELD

The present invention relates to sensors that are implantable into a patient's body, and to systems and methods of using the same.

BACKGROUND

Tracking of physical disease and healing in humans often involves measuring anatomical properties of a patient's body. However, some measurements, such as those that can only be obtained internally, can be difficult to obtain. More recently, there has been an interest in sensors that can be implanted into a patient's body to track the health of the patient over time. For example, attempts have been made to use one or more strain gauges to track healing in a damaged or fractured bone. The one or more strain gauges are attached to an orthopedic implant that is in turn attached to the damaged or fractured bone. As the bone heals, the bone increasingly shares the load imparted by the patient's body on the orthopedic implant. Thus, the load imparted on the bone increases as the bone heals, while the load imparted on the orthopedic implant decreases. In principle, this change in loading can be measured over time by the one or more strain gauges to track the progress of healing in the bone. The measurement can then be communicated to a device outside of the body that can be accessed by a physician.

SUMMARY

In one example, a sensor that is configured to be implanted into a patient's body comprises at least one sensing element, a measurement device in communication with the at least one sensing element, and an internal wireless communicator in communication with the measurement device. The at least one sensing element includes a resistor, and the measurement device includes at least one capacitor. Further, the measurement device is configured to measure a discharge time of the at least one capacitor through the resistor so as to generate a measurement value that is proportional to a value of an anatomical property of the anatomical body observed by the sensor. The wireless communicator is configured to wirelessly communicate the measurement value through skin of the patient to an external wireless communicator situated outside of the patient's body.

In another example, a method detects a value of an anatomical property of a patient from at least one sensor implanted into a patient's body. The method comprises a step of charging at least one capacitor of the at least one sensor to a reference voltage. The method further comprises a step of discharging the at least one capacitor through at least one resistive sensing element of the at least one sensor. The method yet further comprises a step of generating a measurement value that is proportional to the value of the anatomical property. The generating step comprises measuring a discharge time of the at least one capacitor to a trigger voltage. The method yet still further comprises a step of wirelessly communicating the measurement value through skin of the patient to an external wireless communicator situated outside of the patient's body.

In yet another example, a sensor that is configured to be implanted into a patient's body comprises a semiconductor strain gauge with the at least one sensing element, a measurement device in communication, and an internal wireless communicator in communication with the measurement device. The strain gauge has a substrate and first, second, and third sensing elements arranged on the substrate such that the first, second, and third sensing elements are non-parallel to one another. The measurement device is configured to generate a measurement value that is proportional to a value of an anatomical property of the anatomical body observed by the sensor. The wireless transmitter is configured to wirelessly communicate the measurement value through the skin of the patient to an external wireless communicator situated outside of the patient's body.

In yet still another example, a system comprises an anatomical implant and first and second sensors supported by the anatomical implant. The first sensor includes a first unique identifier and comprises at least a first sensing element, a first measurement device in communication with the at least first sensing element, and a first internal wireless communicator. The first measurement device is configured to generate a first measurement value that is proportional to a value of an anatomical property of the anatomical body observed by the first sensor, and the first internal wireless communicator is configured to wirelessly communicate the first measurement value and first unique identifier through skin of a patient's body to an external wireless communicator situated outside of the patient's body. The second sensor includes a second unique identifier, different from the first unique identifier, and comprises at least a second sensing element, a second measurement device in communication with the at least second sensing element, and a second internal wireless communicator. The second measurement device is configured to generate a second measurement value that is proportional to a value of an anatomical property of the anatomical body observed by the second sensor, and the second internal wireless communicator is configured to wirelessly communicate the second measurement value and second unique identifier through skin of a patient's body to the external wireless communicator situated outside of the patient's body.

BRIEF DESCRIPTION OF THE DRAWINGS

The foregoing summary, as well as the following detailed description of embodiments of the application, will be better understood when read in conjunction with the appended drawings. For the purposes of illustrating the methods and bone screws of the present application, there is shown in the drawings representative embodiments. It should be understood, however, that the application is not limited to the precise methods and devices shown. In the drawings.

DETAILED DESCRIPTION

Conventional sensors proposed for use in implantation into a patient's body have several drawbacks. First, conventional sensors tend to have relatively high power needs in order to obtain the level of sensitivity and accuracy needed for the application. Typically, these needs are met with relatively large batteries. However, large batteries are generally not preferred for implantation because they may contain materials that are harmful to the human body and therefore not biocompatible. Further, use of large batteries can impede miniaturization of the sensor. Therefore, there is a need for sensors having relatively low power needs that can be met with smaller batteries or through energy harvesting techniques, while still providing sufficient sensitivity and accuracy.

Disclosed herein are sensors that are configured to be implanted into a patient's body and components thereof. Further, disclosed herein are systems that comprise an anatomical implant and at least one sensor configured to be supported by the anatomical implant. Yet further, disclosed herein are methods of operating such sensors and systems.

Figure 1:
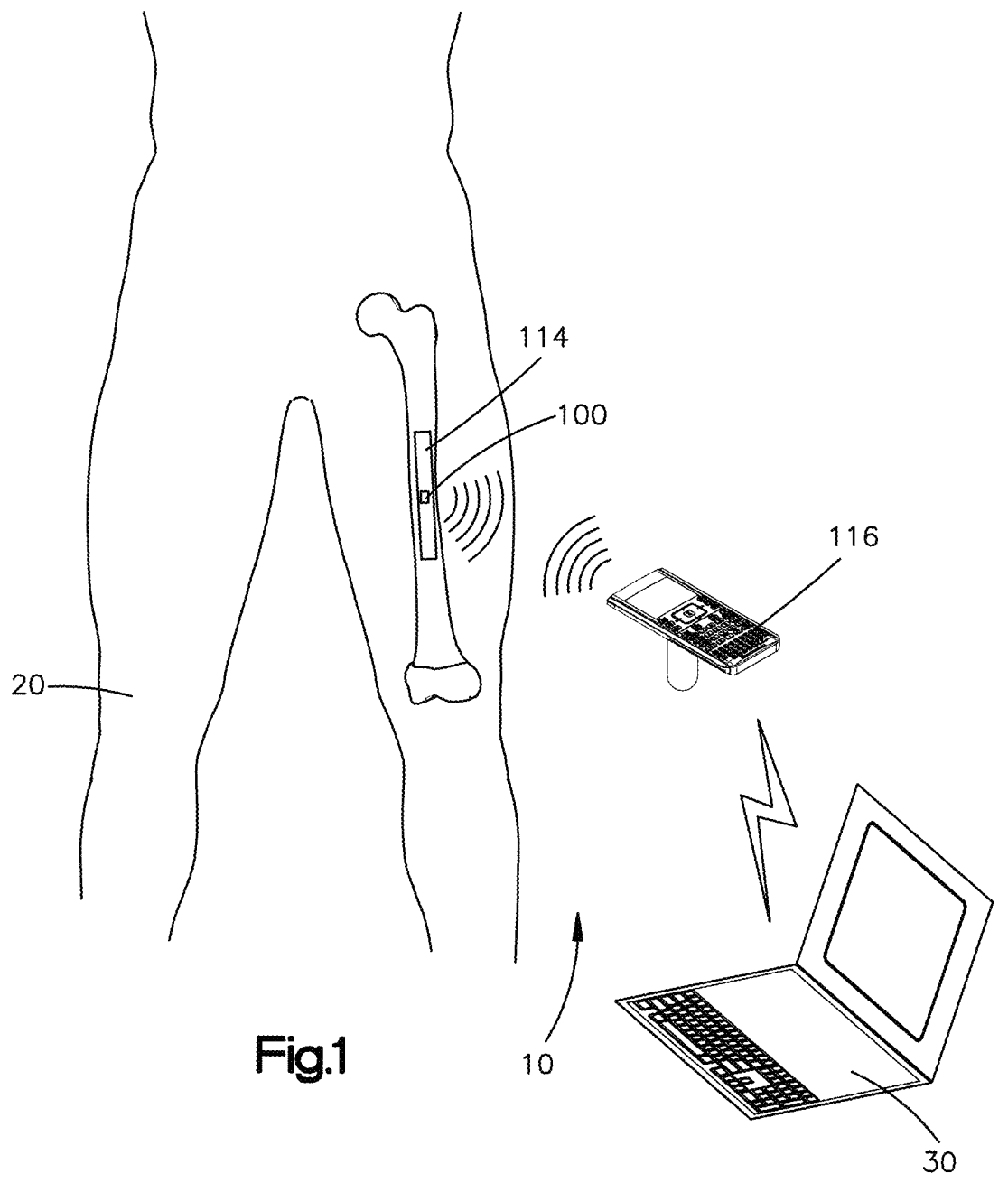
FIG. 1 shows a simplified schematic diagram of a measurement system according to one example embodiment that is positioned relative to a patient so as to measure an anatomical condition of the patient, the system having a sensor supported by an anatomical implant and having an external reader that receives measurements from the sensor.

Referring to FIG. 1, a system 10 is shown that is configured to track health of a patient over time. In general, the system 10 comprises at least one implantable sensor 100 that is configured to be implanted into a patient's body 20. The system can also comprise an anatomical implant 114 configured to support the at least one sensor 100. The anatomical implant 114 can be any suitable anatomical implant such as (without limitation) a bone plate, an intramedullary nail, a bone anchor, a pedicle screw, a spine rod, an intervertebral implant, and so on. In addition, the bone plate can comprise any suitable implantable material such as, without limitation, a metal such as titanium or a polymer such as polyether ether ketone (PEEK). Alternatively, the at least one sensor 100 can be configured to attach directly to an anatomical body of the patient without being supported by an anatomical implant.

The system can further comprise an external wireless reader 116 configured to wirelessly receive data from the at least one sensor 100 through the skin of the patient when the external wireless reader 116 is situated outside of the patient's body. The data can then be communicated to a computing device 30 that can be accessed by the patient or a medical professional. The computing device 30 can be physically separate from the external wireless reader 116 as shown or can be implemented as part of the external wireless reader 116.

In at least some embodiments, the external wireless reader 116 can be configured to wirelessly provide a source of power to the at least one sensor 100. It will be understood that systems of the invention may comprise as few as two, and up to all three, of (1) the at least one sensor 100, (2) the anatomical implant 114, and (3) the external wireless reader 116. Further, it will be understood that various embodiments of the invention can include only one of (1) the at least one sensor 100, (2) the anatomical implant 114, and (3) the external wireless reader 116, as these components can be distributed separately.

Figure 2:
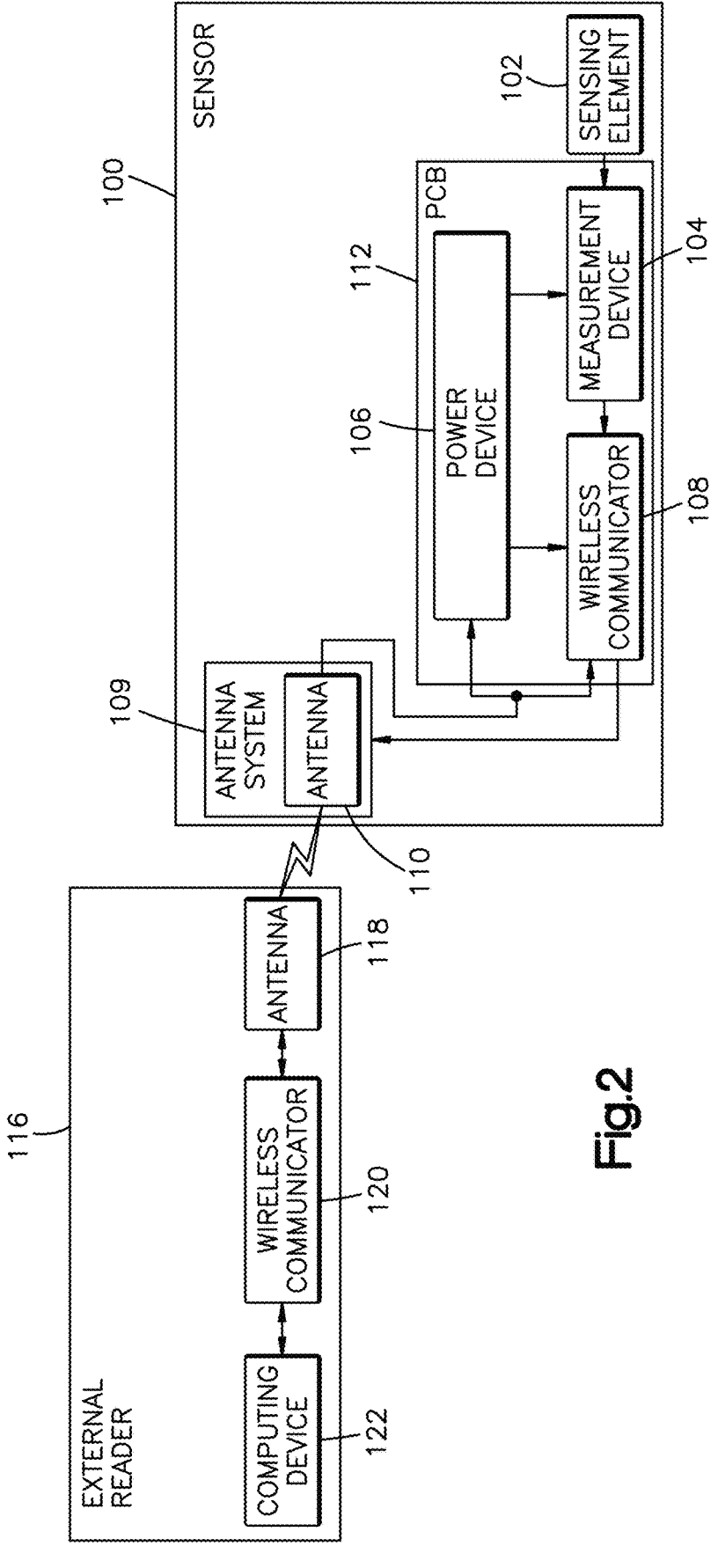
FIG. 2 shows a simplified block diagram of the system of FIG. 1 according to one example embodiment.

Referring now to FIG. 2, a simplified block diagram of the system of FIG. 1 is shown according to one embodiment. The system comprises a sensor 100 that comprises at least one sensing element 102, and a measurement device 104 in communication with the at least one sensing element 102. Together, the at least one sensing element 102 and measurement device 104 are configured to generate a measurement value that is proportional to a value of an anatomical property that a patient's body observed by the at least one sensing element 102 when the sensor 100 is implanted in the patient's body. The anatomical property can be any suitable property for tracking the health of a patient such as (without limitation) strain, load, deflection, rotation, temperature, pressure, pH level, oxygen level, and so on.

To generate the measurement value, each sensing element 102 has a sensor property having a value that changes in response to a change in a value of the anatomical property observed by the sensing element 102. Thus, each sensing element 102 has a sensor property having a value that is proportional to the value of the anatomical property. For example, the sensor property can be resistance, capacitance, inductance, piezoelectricity, light behavior, or other suitable sensor property. The measurement device 104 is configured to detect or measure the value of the sensor property, and the value of the anatomical property can be calculated from the value of the sensor property. In some embodiments, the value of the anatomical property can be calculated by multiplying the measured value of the sensor property by a constant.

Each sensing element 102 can be any suitable type of sensing element for tracking the health of a patient, and the sensor property can be any suitable sensor property. For example, the sensing element can be (without limitation) at least one of a resistive sensing element having a resistance that changes in response to a change in the anatomical property, a piezoelectric sensing element having a piezoelectric material that changes an electrical charge in response to a change in the anatomical property, a capacitive sensing element having a capacitance that changes in response to a change in the anatomical property, an inductive sensing element having an inductance that changes in response to a change in the anatomical property, an optical sensing element, and so on. In one example, and as will be discussed further below, each sensing element 102 can be a resistive sensor, the sensor property of each sensing element 102 can be an electrical resistance of the sensing element 102, and the anatomical property can be strain on the anatomical body, where the resistance of each sensing element 102 changes in response to a change in strain on the anatomical body.

The sensor 100 can comprise an internal wireless communicator 108 in communication with the measurement device 104, and an antenna system 109 in communication with the internal wireless communicator 108. The antenna system 109 can include an antenna 110, and optionally can include other components such as a shield as will be described in further detail below. The internal wireless communicator 108 is configured to receive the measurement value from the measurement device 104 and provide the measurement value to the antenna 110 in a suitable form for wireless transmission. The internal wireless communicator 108 can include a wireless transmitter or transponder that receives the measurement value from the measurement device 104 and prepares the measurement value for wireless transmission. For example, the wireless communicator 108 can include processing such as (without limitation) one or more of (i) memory configured to store the measurement value, (ii) a digital-to-analog converter configured to convert the measurement value to analog format, (iii) a radio-frequency (RF) modulator configured to modulate the measurement value, (iv) an error-correction encoder configured to encode the measurement value, and other processing consistent with the wireless technology employed by the sensor 100.

In one example, the internal wireless communicator 108 can be configured as a passive radio-frequency identification (RFID) transponder. Alternatively, the internal wireless communicator can be configured using any other wireless communication technology suitable for communicating through the skin such as (without limitation) battery-assisted passive RFID, active RFID, Bluetooth, and Wi-Fi. The wireless communicator 108 can further include a unique identifier (ID) that can be used to distinguish the sensor 100 from other sensors. In one example, the unique ID can be an ID of an RFID tag. The antenna 110 is configured to convert an electrical signal corresponding to the measurement value from the wireless communicator 108 into radio waves so as to transmit the measurement value wirelessly through the patient's skin to the external wireless reader 116 situated outside of the patient's body.

The sensor 100 can comprise a power device 106 configured to supply power to the measurement device 104 and wireless communicator 108. In at least some examples, the power device 106 can include an energy harvesting device configured to capture energy from a suitable energy source that is separate from the sensor 100. For example, the energy source can be radio waves communicated from the external wireless reader 116. Alternatively, the power device 106 can capture energy from the patient's body itself or from another external source such as a source external to the patient's body. For example, the energy source can include (without limitation) kinetic energy, electric fields, magnetic fields, and so on. In some embodiments, the power device 106 can include a battery.

The measurement device 104, power device 106, and wireless communicator 108 can each be implemented on a printed circuit board (PCB) 112, although embodiments of the disclosure are not so limited. Further, the measurement device 104, power device 106, and wireless communicator 108 can each be implemented as an integrated circuit (i.e., chip) that is mounted onto the printed circuit board 112. The at least one sensing element 102, printed circuit board 112, and antenna 110 can all be supported by the anatomical implant 114 (shown in FIG. 1), which in turn can be attached to an anatomical body of the patient. Alternatively, the at least one sensing element 102, printed circuit board 112, and antenna 110 can all be attached directly to the anatomical body of the patient.

The external wireless reader 116 is configured to wirelessly receive the measurement value from the at least one sensor 100 through the skin of the patient when the external wireless reader 116 is situated outside of the patient's body. Moreover, in at least some examples, the external wireless reader 116 can be configured to wirelessly provide a source of power to the at least one sensor 100. In at least one such example, the external wireless reader 116 can be implemented as an RFID reader.

The external wireless reader 116 can include an antenna 118 and a wireless communicator 120. The wireless communicator 120 can include a transmitter and a receiver. Thus, the communicator 120 can be considered to be a transceiver. In at least some embodiments, the external wireless reader 116 can further include a computing device 122. The computing device 122 can be configured to calculate a value of the anatomical property based on the measurement value. In one example, the computing device 122 can calculate the value of the anatomical property by multiplying the measurement value by a specified constant. Alternatively, the computing device 122 can be implemented separately from the external wireless reader 116. For example, the computing device 122 can be a computer configured to receive the measurement value from the external wireless reader 116 and present the value to a physician.

Figures 3, 4, 5:
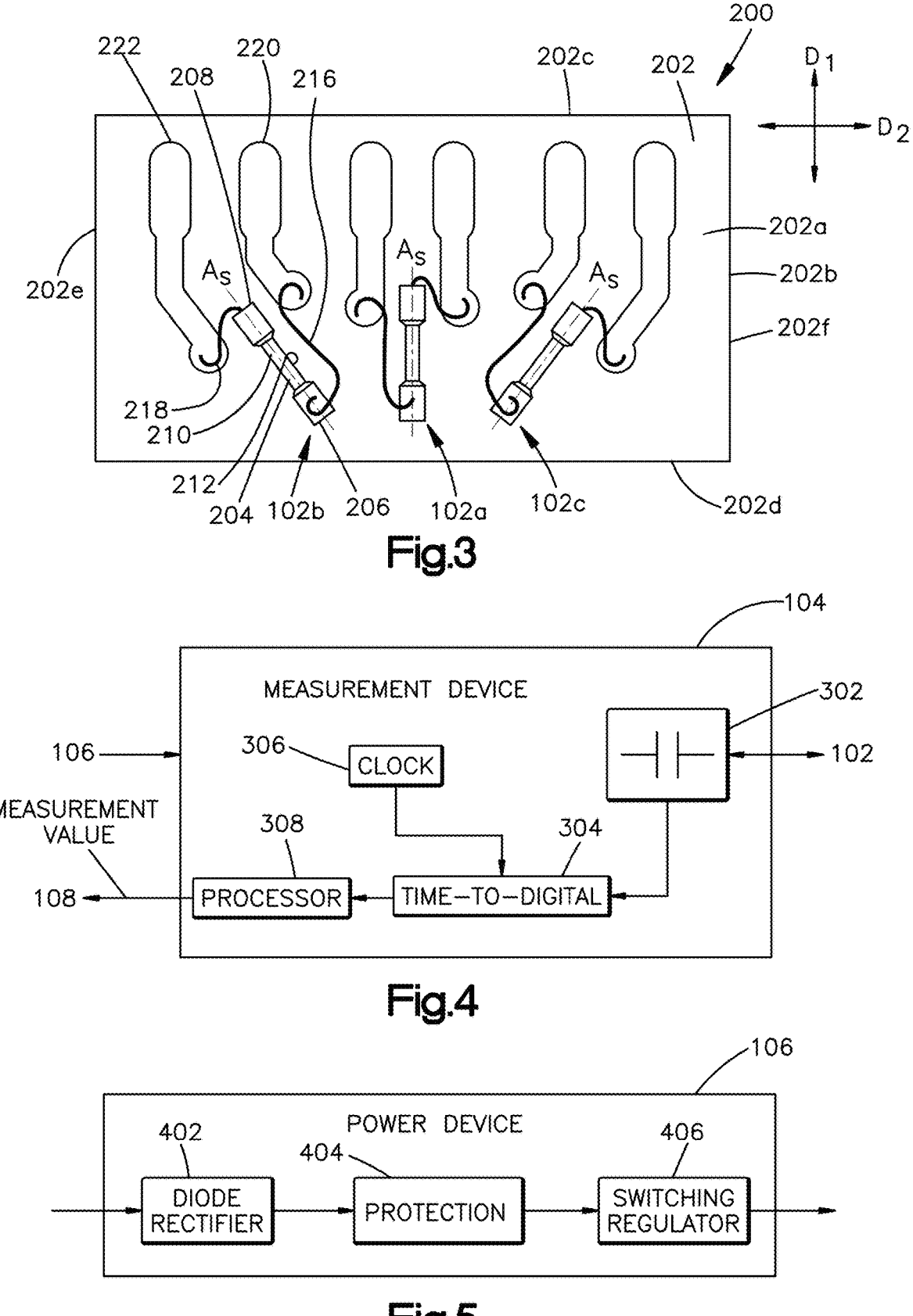
FIG. 3 shows a plan view of a strain gauge according to one example embodiment that can include the at least one sensing element of the sensor of FIG. 2.
FIG. 4 shows a simplified block diagram of the measurement device of the sensor of FIG. 2 according to one example embodiment.
FIG. 5 shows a simplified block diagram of the power device of the sensor of FIG. 2 according to one example embodiment.

Referring to FIGS. 2 and 3, in one example, the sensor 100 can comprise a strain gauge 200 having the at least one sensing element 102. Thus, the at least one sensing element 102 can be part of the strain gauge 200. Each of the at least one sensing element 102 can include a resistor 204. The strain gauge 200 can further include a substrate 202 that carries the at least one sensing element 102. Each of the at least one sensing element 102 can be a semiconductor bar-type strain gauge similar to those manufactured by Micron Instruments, where the semiconductor bar-type strain gauges are arranged on the substrate 202. The substrate 202 can be silicon or any other suitable substrate material. The substrate 202 can be flexible. For example, the substrate 202 can be implemented as a flexible printed circuit board. In at least some embodiments, each of the at least one sensing element 102 can have a gauge factor in the range of 100 to 200. Further, in at least some such embodiments, each of the at least one sensing element 102 can have a gauge factor in the range of 140 to 160. The effective gauge factor can be adjusted by adding resistors (not shown) in series with the strain gauge 200.

The substrate 202 can have a first broadside 202a and a second broadside 202b opposite the first broadside 202a. The substrate 202 can further have a first edge 202c and a second edge 202d opposite one another with respect to a first direction $D_1$. The substrate can yet further have a third edge 202e and a fourth edge 202f opposite one another with respect to a second direction $D_2$, perpendicular to the first direction $D_1$. The first and second broadsides 202a and 202b can extend between the first and second edges 202c and 202d and between the third and fourth edges 202e and 202f The first broadside 202a can be planar along the first and second directions $D_1$ and $D_2$. Similarly, the second broadside 202b can be planar along the first and second directions $D_1$ and $D_2$. The first and second broadsides 202a and 202b can be opposite one another with respect to a third direction $D_3$, perpendicular to both the first and second directions $D_1$ and $D_2$.

The strain gauge 200 can have a height from the first edge 202c to the second edge 202d with respect to the first direction $D_1$. The strain gauge 200 can further define a width from the third edge 202e to the fourth edge 202f with respect to the second direction $D_2$. The strain gauge 200 can yet further define a thickness from the first broadside 202a to the second broadside 202b with respect to the third direction $D_3$. The height and width can be greater than the thickness.

Each of the at least one sensing element 102 can be supported by the substrate 202, such as at the first broadside 202a of the substrate 202. Each of the at least one sensing element 102 can have a first end 206 and a second end 208 spaced from one another along a central axis As of the at least one sensing element 102. Each sensing element 102 can further include a first side 210 and a second side 212 spaced from one another along a direction, perpendicular to the central axis As. The first and second sides 210 and 212 can extend from the first end 206 to the second end 208. Further, each sensing element 102 can be solid from the first end 206 to the second end 208 and from the first side 210 to the second side 212. Each sensing element 102 can have a length from its first end 206 to its second end 208 that is greater than a width of the sensing element 102 from its first side 210 to its second side 212. Thus, each sensing element 102 can have a linear shape and can be elongate from its first end 206 to its second end 208.

The resistor 204 of each sensing element 102 can be disposed between the first end 206 and the second end 208 of the sensing element 102. Further, the resistor 204 can be disposed between the first side 210 and the second side 212 of the sensing element 102. In at least some embodiments, each resistor 204 can be a linear bar that defines one or more, up to all, of the first end 206, the second end 208, the first side 210, and the second side 212 of the corresponding sensing element 102. The strain gauge 200 can be configured to flex so as to allow each sensing element 102 to stretch and compress. Each sensing element 102 can have a resistance that increases as the sensing element 102 is stretched along its central axis As and decreases as the sensing element 102 is compressed along its central axis As.

In alternative embodiments, each of the at least one sensing element 102 can be any suitable gauge such as a U-gauge, wherein the sensing element has a U-shape, or an M-gauge, where the sensing element has an M-shape. Further, each of the at least one sensing element 102 can be implemented using a resistive foil gauge in lieu of a semiconductor gauge. However, semiconductor gauges may enable higher gauge factors than resistive foil gauges, which may result in more accurate readings of low strain values.

The at least one sensing element 102 can include at least first and second sensing elements 102a and 102b. The first and second sensing elements 102a and 102b can be angularly offset from one another so as to be non-parallel to one another. In particular, the central axis As of the first sensing element 102a can be angularly offset from the central axis As of the second sensing element 102b by an angle other than zero or 180 degrees. Further, the longitudinal axes As of the first and second sensing elements can intersect one another. In at least some embodiments, the first and second sensing elements 102a and 102b can be angularly offset from one another by an angle within a range from approximately 30 degrees to approximately 120 degrees. In at least some of such embodiments, the first and second sensing elements 102a and 102b can be angularly offset from one another by an angle in a range from approximately 30 degrees to approximately 90 degrees. In yet still some of such embodiments, the first and second sensing elements 102a and 102b can be angularly offset from one another by an angle in a range of approximately 45 degrees to 60 degrees. In a preferred embodiment, the first and second sensing elements 102a and 102b can be angularly offset from one another by an angle of 45 degrees or 60 degrees.

The at least one sensing element 102 can optionally include at least a third sensing element 102c. The third sensing element 102 can be angularly offset from both the first and second sensing elements 102a and 102b so as to be non-parallel with the first and second sensing elements 102a and 102b. In particular, the central axis As of the third sensing element 102c can be angularly offset from the longitudinal axes As of the first and second sensing elements 102a and 102b by an angle other than zero or 180 degrees. Further, the longitudinal axes As of the first, second, and third sensing elements 102a, 102b, and 102c can intersect one another. The first sensing element 102a can be disposed between the second and third sensing elements 102b and 102c. In at least some embodiments, the central axis As of the first sensing element 102a can be aligned with the first direction $D_1$. In at least some embodiments, the first and third sensing elements 102a and 102c can be angularly offset from one another by an angle within a range from approximately 30 degrees to approximately 120 degrees. In at least some of such embodiments, the first and third sensing elements 102a and 102c can be angularly offset from one another by an angle in a range from approximately 30 degrees to approximately 90 degrees. In yet still some of such embodiments, the first and third sensing elements 102a and 102c can be angularly offset from one another by an angle in a range of approximately 45 degrees to 60 degrees. In a preferred embodiment, the first and third sensing elements 102a and 102c can be angularly offset from one another by an angle of 45 degrees or 60 degrees.

Further, in at least some embodiments, the angle between the first and second sensing elements 102a and 102b can be substantially equal to the angle between the first and third sensing elements 102a and 102c. In some embodiments, each of the first to third second sensing elements 102a to 102c can be offset from an adjacent one of the first to third sensing elements 102a to 102c by an angle in a range from approximately 30 to approximately 120 degrees. In at least some of such embodiments, each of the first to third sensing elements 102a to 102c can be angularly offset from an adjacent one of the first to third sensing elements 102a to 102c by an angle in a range from approximately 30 degrees to approximately 90 degrees. In yet still some of such embodiments, each sensing element 102 can be offset from an adjacent sensing element by an angle in a range of approximately 45 degrees to approximately 60 degrees. In a preferred embodiment, the each sensing element 102 is angularly offset from an adjacent sensing element by an angle of 45 degrees or 60 degrees.

As shown in FIG. 3, the first to third sensing elements 102a to 102c can be arranged on the substrate 202 in a rosette configuration. Arranging the first to third sensing elements 102a to 102c in a rosette configuration can make it easier to determine principal strain from the output of the strain gauge 200. However, it will be understood that embodiments of the disclosure can have as few as one of the sensing elements 102a, 102b, and 102c.

The strain gauge 200 can include a plurality of electrical leads and contact pads. For example, each sensing element 102a, 102b, and 102c can be associated with a first electrical lead 216 and a first contact pad 220. Each first electrical lead 216 and each first contact pad 220 can be arranged on the substrate 202. Each first electrical lead 216 can extend from the first end 206 of its associated sensing element 102a, 102b, or 102c to a corresponding one of the first contact pads 220 so as to electrically couple the first end 206 and the first contact pad 220. Each first contact pad 220 can be configured to electrically connect to a conductor of the measurement device 104, such as a pin or terminal of the measurement device 104, so as to place the corresponding sensing element 102a, 102b, or 102c in electrical communication with the measurement device 104.

Similarly, each sensing element 102a, 102b, and 102c can be associated with a second electrical lead 218 and a second contact pad 222. Each second electrical lead 218 and each second contact pad 222 can be arranged on the substrate 202. Each second electrical lead 218 can extend from the second end 208 of its associated sensing element 102a, 102b, or 102c to a corresponding one of the second contact pads 222 so as to electrically couple the second end 208 and the second contact pad 222. Each second contact pad 222 can be configured to electrically connect to a conductor of the measurement device 104, such as a pin or terminal of the measurement device 104, so as to place the corresponding sensing element in electrical communication with the measurement device 104. Each resistor 204 can have a width along a direction that is perpendicular to its axis As, the width being greater than a corresponding width of the electrical leads 216 and 218.

Referring back to FIG. 2, in some embodiments, the measurement device 104 can generate the measurement value by directly measuring the resistance of each resistor of the at least one sensing element 102. Further, the value of the anatomical property observed by the at least one sensing element 102 can be calculated based on the measured resistance. However, measurement devices that measure resistance directly can have relatively high power needs, and as a result, may need to be powered using relatively large batteries. Thus, measurement devices that measure resistance may be less suitable for use with energy harvesting or passive wireless technologies such as passive RFID, and might not be conducive to miniaturization for implantation into a patient's body.

In alternative embodiments, the measurement device 104 can measure resistance indirectly by measuring a property other than resistance but that is indicative of resistance. For example, FIG. 4 shows an example embodiment of the measurement device 104 of FIG. 2. The measurement device 104 can include at least one capacitor 302, and the measurement device 104 can be configured to measure a discharge time of the at least one capacitor 302 through the resistor of the at least one sensing element 102 to generate the measurement value. The measurement device 104 can comprise a PicoStrain® integrated circuit manufactured by Acam Messelectronic Gmbh. Further, the measurement device 104 can be used with the strain gauge 200 of FIG. 3 or any other suitable resistive sensing element, including resistive sensing elements that measure an anatomical property other than strain.

In one example, the measurement device 104 can include a single capacitor for all of the sensing elements 102. Accordingly, the measurement device 104 can measure the discharge time for the sensing elements 102 sequentially. A separate measurement result can be produced for each of the at least one sensing elements 102, and the measurement results can be transmitted outside of the body for calculation of principal strain. Alternatively, the measurement device 104 can calculate the principal strain.

The amount of time that it takes for the at least one capacitor 302 to discharge through the resistor of the at least one sensing element 102 is proportional to the resistance of the resistor. Thus, as the resistance of the resistor increases, the discharge time of the at least one capacitor 302 increases. Further, as the resistance of the resistor decreases, the discharge time of the at least one capacitor 302 decreases. Since the discharge time of the at least one capacitor 302 is proportional to the resistance of the resistor of the at least one sensing element 102, and since the resistance of the resistor of the at least one sensing element 102 is proportional to the value of the anatomical property observed by the at least one sensing element 102, the discharge time is also proportional to the value of the anatomical property observed by the at least one sensing element 102. As a result, the value of the anatomical property observed by the at least one sensing element 102 can be calculated based on the discharge time of the at least one capacitor 302. Thus, when the measurement device 104 is used with a strain gauge such as in FIG. 3, the discharge time is proportional to strain observed by the at least one sensing element 102, and the strain can be calculated based on the discharge time.

The measurement device 104 can include a time-to-digital converter 304 that is in communication with the at least one capacitor 302. The time-to-digital converter 304 can be configured to measure the discharge time of the at least one capacitor 302 as the at least one capacitor 302 discharges from a reference voltage (e.g., Vcc) down to a trigger voltage level. The sensor 100 can include a clock 306 that provides a clock signal to the time-to-digital converter 304. The clock 306 can be implemented as part of the measurement device 104 or can be implemented separate from the measurement device 104. In operation, the power device 106 charges the capacitor 302 to the reference voltage, and the capacitor 302 is discharged through the resistor of the at least one sensing element 102 down to the trigger voltage level. As the capacitor 302 is discharged, the time-to-digital converter 304 increments a counter in response to the clock signal to count the time that it takes for the capacitor 302 to discharge to the trigger voltage level. Thus, the measurement device 104 can be configured to generate a measurement of discharge time.

In at least some embodiments, the measurement value output by the measurement device 104 can be the discharge time measured by the measurement device 104. Alternatively, the measurement value can be a value that is proportional to the discharge time. Alternatively still, the measurement value output by the measurement device 104 can be the value of the anatomical property, and can be calculated based on the discharge time measured by the measurement device 104. In at least one embodiment, the sensor 100 can include at least one processor 308 configured to calculate the value of the anatomical property based on the measured discharge time. For example, the processor 308 can multiply the measured discharge time by a specified constant to obtain the value of the anatomical property. Alternatively, the at least one processor 308 can be implemented downstream of the measurement device 104, but upstream of the antenna 110, or at an external device outside of the patient's body such as at the reader 116 or the computing device 30 (see FIG. 1).

Measuring the discharge time of the at least one capacitor 302 can be performed using significantly less power than measuring the resistance directly. Accordingly, the measurement device 104 of FIG. 4 can be implemented with lower power devices such as energy harvesting devices and passive powering devices. For example, the measurement device 104 and wireless transceiver 108 can be operated with power as low as 10 mW. Despite receiving less power, the measurement device 104 may still be capable of obtaining accurate readings of low strain values. Further, the measurement device 104 may be capable of obtaining accurate readings at depths in the body from 0 cm beneath the skin up to 15 cm beneath the skin.

Referring to FIGS. 2 and 5, the power device 106 can be configured to supply power to the measurement device 104. In FIG. 5, an example embodiment of the power device 106 of FIG. 2 is shown in which the power device 106 is an energy-harvesting power device. In general, the energy-harvesting power device 106 is configured to capture the energy from the radio waves received by the antenna 110 and supply power to the wireless communicator 108 and the measurement device 104. For example, the energy-harvesting device 106 can supply power to components of the measurement device 104 such as the capacitor 302, time-to-digital converter 304, clock 306, and processor 308.

The energy-harvesting power device 106 can include a rectifier 402 configured to allow current received from the antenna 110 to pass in one direction to processing downstream of the rectifier 402. The rectifier 402 can be configured to convert alternating current from the antenna 110 into direct current that is provided to processing downstream of the rectifier 402. The rectifier 402 can be a diode rectifier or any other suitable rectifier.

The energy-harvesting power device 106 can include a protection circuit 404 configured to receive the energy output by the rectifier 402 and provide a reduced voltage output to processing downstream of the protection circuit 404. The energy-harvesting power device 106 can include a regulator 406 configured to receive the reduced voltage output from the protection circuit 404 and output a regulated power supply to the measurement device 104 and wireless communicator 108. The regulator 406 can be a switching regulator or any other suitable regulator including (without limitation) a linear regulator.

Figure 6:
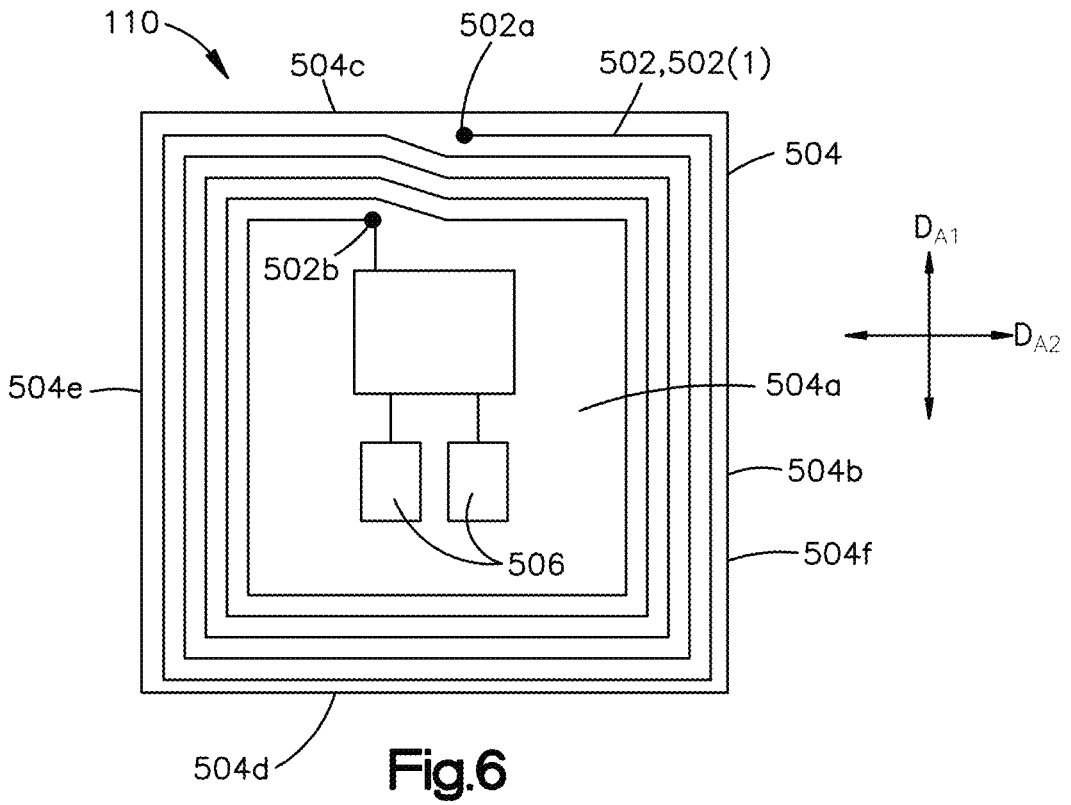
FIG. 6 shows a plan view of the antenna of the sensor of FIG. 2 according to one example embodiment.

FIG. 6 shows an example embodiment of the antenna 110 of FIG. 2. The antenna 110 can include a substrate 504 and at least one inductive coil 502 arranged on the substrate 504. The substrate 504 can be a film or other suitable substrate.

In one example, the antenna 110 can be implemented as a flexible printed circuit board. The substrate 504 can have a first broadside 504a and a second broadside 504b opposite the first broadside 504a. The substrate 504 can further have a first edge 504c and a second edge 504d opposite one another with respect to a first direction $D_{A1}$. The substrate 504 can yet further have a third edge 504e and a fourth edge 504f opposite one another with respect to the second direction $D_{A1}$, perpendicular to the first direction $D_{A1}$. The first and second broadsides 504a and 504b can extend between the first and second edges 504c and 504d and between the third and fourth edges 504e and 504f The first broadside 504a can be planar along the first and second directions $D_{A1}$ and $D_{A2}$. Similarly, the second broadside 504b can be planar along the first and second directions $D_{A1}$ and $D_{A2}$. The first and second broadsides 504a and 504b can be opposite one another with respect to a third direction $D_{A3}$, perpendicular to both the first and second directions $D_{A1}$ and $D_{A2}$. Note that the directions $D_{A1}$, $D_{A2}$, and $D_{A3}$ can be aligned with the directions $D_1$, $D_2$, and $D_3$, or can be angularly offset from the directions $D_1$, $D_2$, and $D_3$.

The substrate 504 can have a height from the first edge 504c to the second edge 504d with respect to the first direction $D_{A1}$. The substrate 504 can further define a width from the third edge 504e to the fourth edge 504f with respect to the second direction $D_{A2}$. The substrate 504 can yet further define a thickness from the first broadside 504a to the second broadside 504b with respect to the third direction $D_{A3}$. The overall height and width can be greater than the overall thickness. In some examples, the substrate 504 can have a square shape; however, in alternative examples, the substrate 504 can have any other suitable shape.

Each of the at least one antenna coil 502 can be an electrically conductive wire or trace. Each coil 502 can include a first end 502a and a second end 502b offset from one another. Each coil 502 can extend about a center of the coil 502 in a spiral pattern from the first end 502a to the second end 502b such that the second end 502b is spaced closer to the center of the coil 502 than the first end 502a. Thus, each coil 502 can have a plurality of turns. In at least some examples, the number of turns can be in a range from four turns to 30 turns. Each coil 502 can have an overall shape that is square; however, in alternative embodiments, each coil 502 can have another suitable shape. The antenna 110 can further include a pair of contact pads 506 for each coil 502, each configured to electrically connect to a conductor such as a pin or terminal of one or both of the power device 106 and the wireless communicator 108 so as to place the antenna coil 502 in electrical communication with one or both of the power device 106 and the wireless communicator 108.

In some examples, the at least one antenna coil 502 can include a first antenna coil 502(1) supported at the first broadside 504a, and a second antenna coil 502(2) (discussed and shown below in relation to FIGS. 15-17) supported at the second broadside 504b. The second antenna coil 502(2) can be configured in a manner substantially similar to that discussed above in relation to FIG. 8. In some embodiments, the second antenna coil 502(2) can be shifted such that the turns of the second antenna coil 502(2) are substantially aligned with the gaps in-between the turns of the of the first antenna coil 502(1) with respect to the third direction $D_{A3}$. Shifting the turns of the first antenna coil 502(1) and the second antenna coil 502(2) can limit or reduce the parasitic capacitance between the two antenna coils. Further, shifting the turns of the antenna coils can increase the self-resonant frequency of the coils and decrease losses in the coils. The number of turns of antenna 110 can be divided between the first antenna coil 502(1) and the second antenna coil 502(2). For example, in an antenna having ten turns, the first antenna coil 502(1) and the second antenna coil 502(2) can each have five of the ten turns.

Figures 7, 8, 9:
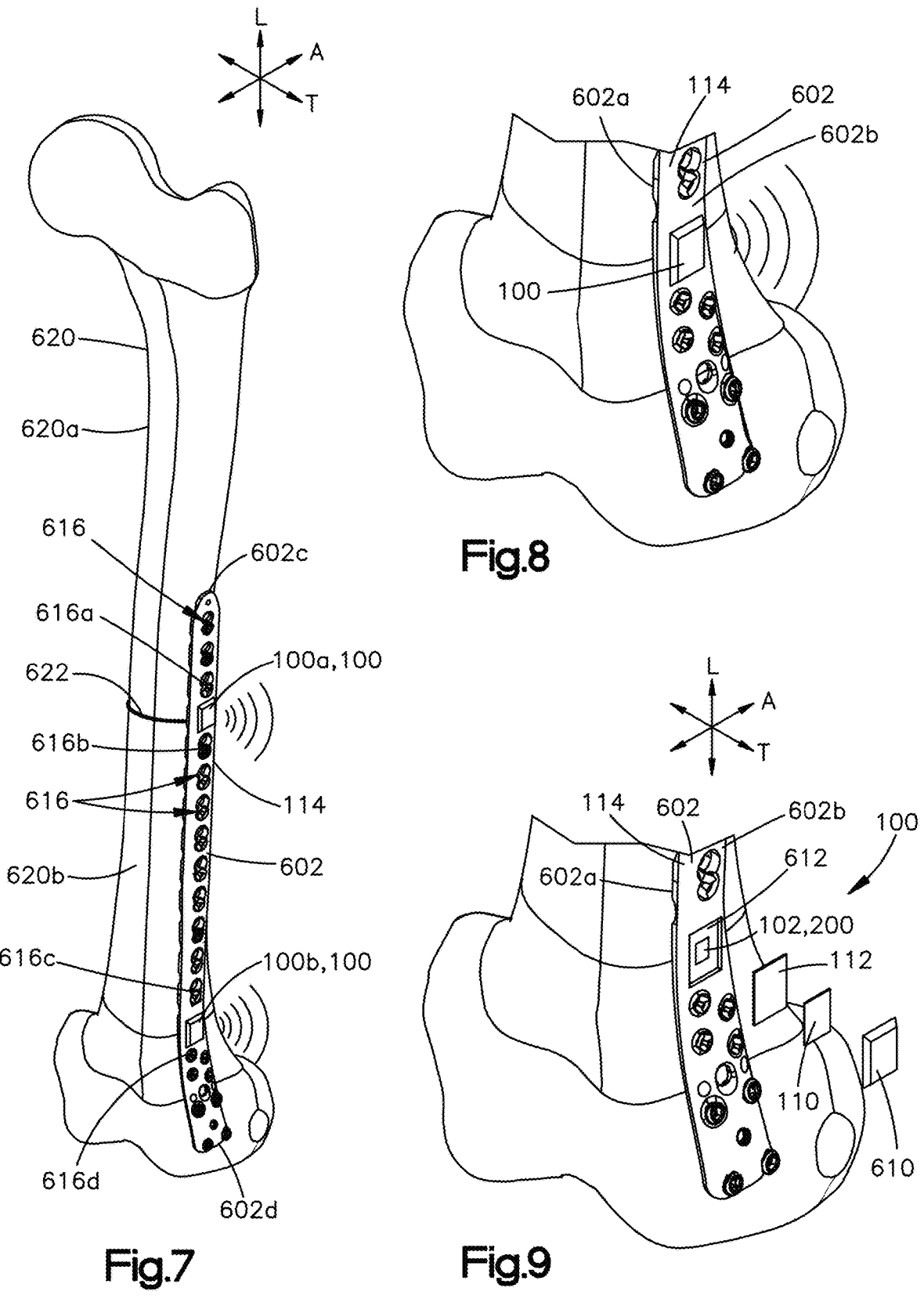
FIG. 7 shows a perspective view of a measurement system attached to an anatomical body according to one example embodiment, the system comprising an anatomical implant and first and second sensors supported by the implant.
FIG. 8 shows an enlarged perspective view of a lower portion of the measurement system of FIG. 7.
FIG. 9 shows a partially-exploded perspective view of the lower portion of the measurement system of FIG. 7.

Turning now to FIGS. 7 to 9, one example of an implantable sensor system is shown. The system comprises an anatomical implant 104 having an implant body 602 and at least one implantable sensor 100. For example, the at least one implantable sensor 100 can include a first sensor 100a and a second sensor 100b. At least one, up to all, of the at least one implantable sensor 100 can be configured to be supported by the anatomical implant body 602. In this example, the anatomical implant 114 comprises a bone plate, and the at least one sensor 100 is configured to track strain imparted by a bone 620 on the implant 114 during healing of the bone 620. The bone 620 has a first portion 620a and a second portion 620b separated by a fracture 622 with respect to a longitudinal direction L. However, as described above in relation to FIGS. 1 and 2, in alternative embodiments, the anatomical implant 114 could be any suitable anatomical implant and the sensor 100 could be any suitable sensor for tracking any suitable anatomical property.

The anatomical implant 114 has a body 602 having an anatomical-body-facing surface 602a and an outer surface 602b opposite the anatomical-body-facing surface 602a along a transverse direction T, perpendicular to the longitudinal direction L. In this example, the anatomical-body-facing surface 602a is a bone-facing surface. The anatomical implant body 602 has a first end 602c and a second end 602d opposite the first end 602c. The first and second ends 602c and 602d can be offset from one another along the longitudinal direction L. Further, first and second ends 602c and 602d can be offset from one another along a central axis $A_I$ of the anatomical implant 114. Thus, in one embodiment, the central axis $A_I$ can extend substantially along the longitudinal direction L; however, in alternative embodiments, the central axis $A_I$ can be bent so as to not extend entirely along the longitudinal direction L. The anatomical implant body 602 has a first side 602e and a second side 602f that are offset from one another along a lateral direction A, perpendicular to both the longitudinal and transverse directions.

The anatomical implant 114 is configured to be attached to a bone using any suitable attachment. For example, the implant 114 can include a plurality of apertures configured to receive bone screws therethrough to attach the implant 114 to the bone. The plurality of apertures 616 can include at least one pair of apertures spaced from one another with respect to the longitudinal direction L. For example, the at least one pair of apertures can include a first pair of apertures that includes a first aperture 616a and a second aperture 616b spaced from one another with respect to the longitudinal direction L. At least one sensor 100a can be disposed between the first and second apertures 616a and 616b. Accordingly, the first and second apertures 616a and 616b can receive bone screws therethrough so as to secure a position of the anatomical implant 114, and hence the at least one sensor 100a, with respect to the longitudinal direction L. In at least one embodiment, the plurality of apertures 616 can include, for each sensor 100 supported by the implant 114, at least one corresponding pair of apertures 616, and each sensor 100 can be disposed between the apertures of its corresponding pair of apertures 616. Each sensor 100 can be disposed between the apertures of its corresponding pair of apertures 616 without any other sensors disposed between the corresponding pair of apertures 616.

The anatomical implant 114 is configured to support at least one of the sensors 100. For example, the anatomical implant body 602 can define at least one recess 612 for each sensor 100 supported by the implant body 602. The recess 612 can extend into the outer surface 602b of the anatomical implant body 602 towards the inner surface 602a. The recess 612 can be configured to receive at least a portion of a corresponding one of the sensors 100 so as to at least partially house the corresponding sensor 100. In alternative embodiments, one or more of the sensors 100 can be mounted to the outer surface 602b of the anatomical implant 602 without being received in a recess such as the recess 612 or can be disposed inside the anatomical implant body 602 between the inner and outer surfaces 602a and 602b.

Each sensor 100 can comprise at least one sensing element 102, a printed circuit board 112, and an antenna 110 as shown in FIG. 9. Further, each of the at least one sensor 100 can include a cover 610. It will be understood that sensors 100a and 100b can each be implemented as shown in FIG. 9. In one example, the at least one sensing element 102 can be part of a strain gauge having a substrate with first and second broadsides and the at least one sensing element in a manner similar to that described above in relation to strain gauge 200 of FIG. 3. The strain gauge can be supported by the anatomical implant body 602 such that the second broadside of the strain gauge 200 is in contact with the anatomical implant body 602. Further, the strain gauge 200 can be supported such that the central axis As of a first one of the sensing elements 102a that extends along the first direction $D_1$ is aligned with the longitudinal direction L of the implant 114. Thus, the first sensing element 102a can be configured so as to detect tensile and compressive forces imparted by the first and second portions 620a and 620b of the bone 620 on the implant 114 along the longitudinal direction L. Further, the strain gauge 200 can be supported such that the third direction $D_3$ of the strain gauge 200 is aligned with the transverse direction T.

The at least one sensing element 102 can further include one or more additional sensing elements supported by the implant body 602 so as to detect one or both of torsional and bending forces imparted by the first and second portions 620a and 620b of the bone 620 on the implant 114. For example, the at least one sensing element 102 can include one or more of the sensing elements 102b and 102c of FIG. 3, which can be angularly offset from the longitudinal direction L so as to detect torsional and bending forces.

The printed circuit board 112 can include a substrate and one or more integrated circuits mounted onto the substrate. Further, the printed circuit board 112 can be configured as described above in relation to printed circuit board 112. For example, the one or more integrated circuits can include an integrated circuit comprising the power device 106, an integrated circuit comprising the measurement device 104, and an integrated circuit comprising the wireless communicator 108. In at least one embodiment, the integrated circuit comprising the power device 106 can be implemented as an energy harvesting chip, the integrated circuit comprising the measurement device 104 can be implemented as a PicoStrain® chip, and the integrated circuit comprising the wireless communicator 108 can be implemented as an RFID chip.

When each of the at least one sensor 100 is assembled, the at least one sensing element 102, the printed circuit board 112, and the antenna 110 can be aligned along the transverse direction T of the implant 114. The transverse direction T can be aligned with third direction $D_3$ of the antenna and the strain gauge. For example, the printed circuit board 112 can be disposed between the at least one sensing element 102 and the antenna 110. One of the first and second broadsides of the at least one sensing element 102 (e.g., one of the first and second broadsides 202a and 202b of the strain gauge 200 of FIG. 3), can face towards one of first and second broadsides of the antenna 110 (e.g., one of first and second broadsides 504a and 504b of FIG. 6). Similarly, one of first and second broadsides of the antenna 110 (e.g., one of first and second broadsides 504a and 504b of FIG. 6) can face towards one of the first and second broadsides of the at least one sensing element 102 (e.g., one of the first and second broadsides 202a and 202b of the strain gauge 200 of FIG. 3). Further, the printed circuit board 112 can have a first broadside that faces the at least one sensing element 102 and a second broadside that is opposite the first broadside along the transverse direction T and that faces the antenna 110.

The cover 610 can be aligned with the at least one sensing element 102, the printed circuit board 112, and the antenna 110 along the transverse direction T direction. Thus, the antenna 110 can be disposed between the printed circuit board 112 and the cover 610 with respect to the select direction. The cover 610 can include an inner side and outer side opposite the inner side along the select direction. In at least one example, the inner side can define a recess that extends therein. Thus, the cover 610 can define a housing having a recess configured to house at least one of the at least one sensing element 102, the printed circuit board 112, and the antenna 110. Alternatively, the recess 612 in the implant body 602 can be deeper so as to receive an entirety of the sensor 100, and the inner side of the cover 610 can be substantially planar without a recess so as to cover the recess 612. The cover can be made from any suitable material. For example, the cover 610 can be made from a biocompatible material, including (without limitation) a biocompatible polymer such as polyether ether ketone (PEEK), a metal, or ceramic. In the assembled configuration, each sensor 100 can have an overall size in a plane perpendicular to the select direction between approximately 8 mm×8 mm and approximately 20 mm×20 mm, and increments of 1 mm therebetween. In one example, each sensor 100 can have an overall size in the plane of approximately 12 mm×12 mm. Each sensor 100 can further have an overall thickness in the select direction between approximately 2 mm and 4 mm.

Turning now to FIGS. 1, 2, 3, 4 and 10, a method of detecting a value of an anatomical property of a patient from the at least one sensor 100 of FIG. 2 implanted into a patient's body is now described. In step 702, the at least one capacitor 302 of the at least one sensor 100 is charged to a reference voltage. For example, the power device 106 can provide power to the at least one capacitor 302. The charging step 702 can comprise capturing energy from a source separate from the at least one sensor 100 at an energy-harvesting device, and providing the energy from the source to the at least one capacitor 302 so as to charge the at least one capacitor 302. The energy source can be radio waves from the reader 116 that excite the antenna coil of the antenna 100 to produce a current in the antenna coil. For example, in the case of RFID, the antenna 110 can receive power from the radio-frequency signal transmitted by the reader 116. In alternative embodiments, the energy source can include (without limitation) kinetic energy, electric fields, magnetic fields, and so on. Alternatively or additionally, the power device 106 can provide power to the at least one capacitor 302 from a battery of the power device 106.

In step 704, the at least one capacitor 302 is discharged through at least one resistive sensing element of the at least one sensor 102. In some embodiments, the discharging step

804 can comprise discharging the at least one capacitor 302 through at least two resistive sensing elements that are non-parallel to one another such as sensing elements 102a and 102b of FIG. 3. Further, in some embodiments, the discharging step 704 can comprise discharging the at least one 302 capacitor through three resistive sensing elements that are non-parallel to one another such as sensing elements 102a, 102b, and 102c of FIG. 3.

In step 706, at least one measurement value is generated that is proportional to the value of the anatomical property. The generating step 706 comprises measuring a discharge time of the at least one capacitor 302 to a trigger voltage. In at least some embodiments, the generating step 706 can comprise measuring the discharge time of the at least one capacitor 302 using a time-to-digital converter 304. Further, the generating step 706 can comprise calculating the measurement value based on the discharge time. However, in some embodiments, the measurement value can be the discharge time. Steps 704 and 706 can be performed for each sensing element in a sequential manner. For example, the at least one capacitor 302 can be discharged through a first one of the sensor elements 102a, 102b, and 102c to generate a first measurement value, then a second one of the sensor elements 102a, 102b, and 102c to generate a second measurement value, and finally through a third one of the sensor elements 102a, 102b, and 102c to generate a third measurement value.

In step 708, the at least one measurement value is wirelessly communicated through skin of the patient to an external wireless communicator situated outside of the patient's body. The wireless communication step 708 can comprise wirelessly communicating the at least one measurement value to the external wireless communicator. Further, the wireless communicating step 708 can comprise communicating a unique ID to the external wireless communicator that identifies the at least one sensor. In the case of RFID, the electronics connected to the antenna 110 can modulate the load seen by the antenna 110 based on the at least one measurement value and optionally the unique ID, and this modulation can be sensed by the reader 116.

Embodiments of the disclosure can further include implants, systems, and methods including at least two sensors. For example, according to various embodiments, the sensors of the present disclosure can be used to implement any of the sensors of U.S. patent application publication 2013/0190654, the teachings of which are hereby incorporated by reference as if set forth in their entirety herein. U.S. patent application publication 2013/0190654 discloses systems including at least two sensors. In general, a first sensor is supported at the fracture site in the bone to measure strain and/or load at the fracture site when the bone is under a given load. As the bone heals, the bone increasingly shares any load imparted by the patient's body on the implant. Thus, the strain or loading imposed on the implant at the first sensor is affected by the strength or stiffness of the weakened bone portion at the fracture. In theory, if the bone were under a constant load, then the load imparted on the bone would increase as the bone heals, while the load imparted on the implant at the first sensor would decrease.

However, the load imparted on the implant might not be constant. Rather the load might vary based on, for example, the amount of load that the patient places on the bone (e.g., the amount of weight that a patient places on a leg). Therefore, a second sensor can be supported at the healthy (i.e., non-damaged) bone to detect the amount of strain or loading that should be experienced by healthy bone when the bone is under the given load. The measured strain or loading from the first sensor at the damaged portion of the bone can then be compared to the measured strain or loading from the second sensor at the healthy portion of the bone.

For example, and with reference to FIGS. 7 and 8, the at least one sensor 100 can include a first sensor 100a configured to be supported by the implant body 602 and a second sensor 100b configured to be supported by the implant body 602. Each sensor 100a and 100b can include a unique ID to distinguish the sensors 100a and 100b from one another. Thus, the first sensor 100a can include a first unique ID, and the second sensor 100b can include a second unique ID, different from the first unique ID. The unique IDs can also be used to distinguish the sensors 100a and 100b from sensors implanted in other patients. The unique IDs can be IDs of RFID tags.

The first and second sensors 100a and 100b can be spaced from one another with respect to the longitudinal direction L. The first sensor 100a can be configured to be supported by the implant body 602 such that, when the implant 114 is attached to the bone 100, the first sensor 100a is disposed adjacent to or over the fracture 622. For example, the first sensor 100a can be aligned with the fracture 622 with respect to the transverse direction T. The first sensor 100a can also be disposed between first and second apertures 616a and 616b that are configured to receive a bone screw therethrough to attach the implant 114 to bone. Thus, the first sensor 100a can be isolated between the first and second apertures 616a and 616b.

The second sensor 100b can be supported by the implant body 602 such that the second sensor 100b is supported over a healthy (e.g., solid) portion 620b of the bone 620. For example, the second sensor 100b can be aligned with the healthy portion 620b with respect to the transverse direction T. The second sensor 100b can also be disposed between first and second apertures 616c and 616d that are configured to receive a bone screw therethrough to attach the implant 114 to bone. Thus, the second sensor 100b can be isolated between the first and second apertures 616c and 616d. The first and second apertures 616a and 616b corresponding to the first sensor 100a can each be spaced from the first and second apertures 616c and 616d corresponding to the second sensor 100b with respect to the longitudinal direction L. Alternatively, one of the apertures 616b and 616c can be shared between the first and second sensors 100a and 100b.

Figures 11, 12:
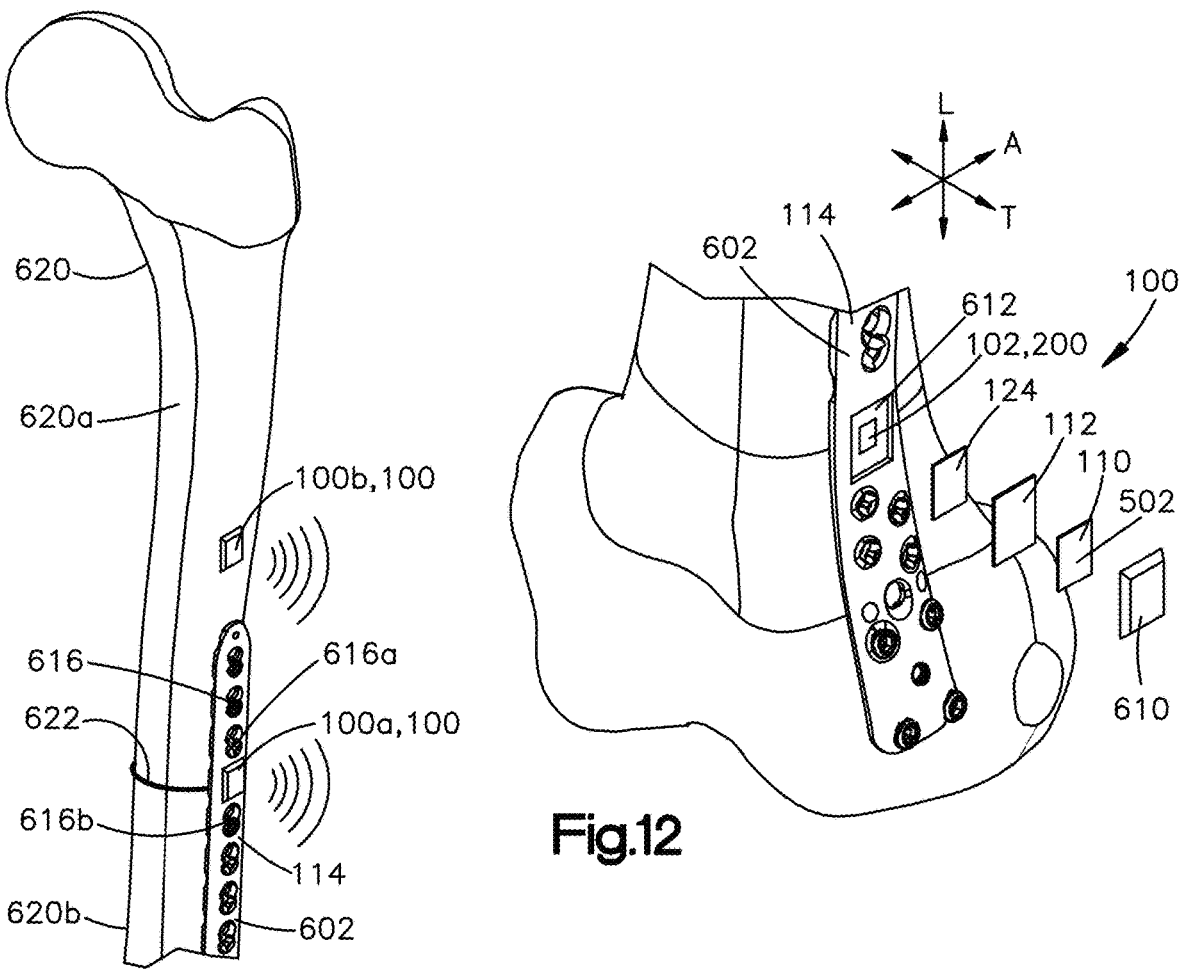
FIG. 11 shows a perspective view of a measurement system attached to an anatomical body according to another example embodiment, the system comprising an anatomical implant, a first sensor supported by the implant, and a second sensor that is not supported by the implant.
FIG. 12 shows an exploded perspective view of a lower portion of a measurement system according to one example embodiment, where the sensor includes a shield disposed between the antenna and the implant.

It will be understood that, as an alternative, loading on the healthy portion 620b of the bone can be detected without the second sensor 100b being supported by the implant 114. For example, as shown in FIG. 11, the loading on the healthy portion 620b can also be detected by attaching the second sensor 100b directly onto the bone 620. As another example, the loading of the healthy portion 620b can be detected by attaching the second sensor 100b to another implant that is in turn attached to the bone 620. The other implant can include, for example, another bone plate, a bone anchor such as a screw, and so on. Thus, according to some alternative embodiments, the system can comprise a first sensor 100a supported by the implant body 602 and a second sensor 100b configured to be attached to the bone 620 so as to be spaced from and separate from the implant 114.

Figure 10:
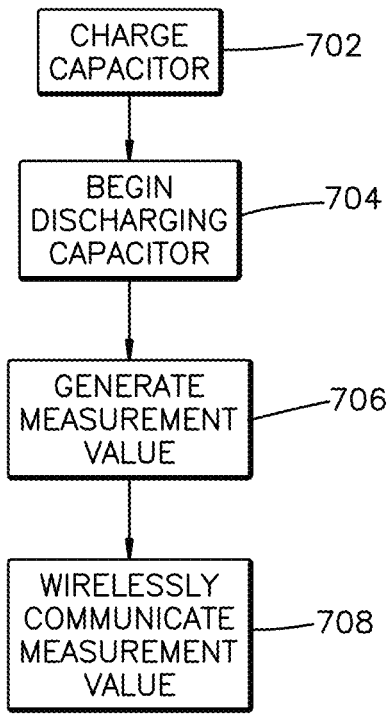
FIG. 10 shows a simplified flow diagram of a method of operating the sensor of FIG. 2 according to one example embodiment.

A method of operating the system of FIGS. 7 and 11 can include performing the method of FIG. 10 for each of the first and second sensors to (i) generate a first measurement value for the first sensor 100a and a second measurement value for the second sensor 100b, and (ii) communicate the first measurement value with the first unique ID and the second measurement value with the second unique ID to the external wireless communication device. The method can further include a step of generating a comparison value based on the first and second measurement values. In one example, the comparison value can be a ratio of one of the first and second measurement values to the other of the first and second measurement values. In another example, the comparison value can be a difference between the first and second measurement values. In yet another example, the comparison can be determined in a look-up table by looking up the first and second measurement values and finding the comparison therein that corresponds to the first and second measurement values.

Referring back to FIGS. 1 and 9, the current of the reader 116 can cause eddy currents in a metallic implant 114. Moreover, as the radio waves excite the antenna coil of the antenna 110 to produce a current in the antenna coil, the antenna coil produces an electromagnetic field that can also excite eddy currents in the metallic implant 114. The eddy currents in turn can decrease the magnetic flux observed by the antenna coil of the antenna 110. Moreover, the eddy currents can rotate in direction opposite the current flow in the antenna coil, thereby opposing the current in the antenna coil of the antenna 110 and changing the tuning frequency of the antenna coil. This interference from the eddy currents can reduce the efficiency of the wireless link between the reader 116 and the sensor 100.

To limit the effect of eddy currents, a ferrite layer (not shown) can be implemented between the antenna 110 and the implant 114. The ferrite layer can prevent at least some of the electro-magnetic field from reaching the metallic implant 114, thus limiting the eddy currents that are excited in the metallic implant 114. However, ferrite is not biologically compatible, and therefore, presents some challenges when being implemented in an implantable sensor.

Figures 13, 14:
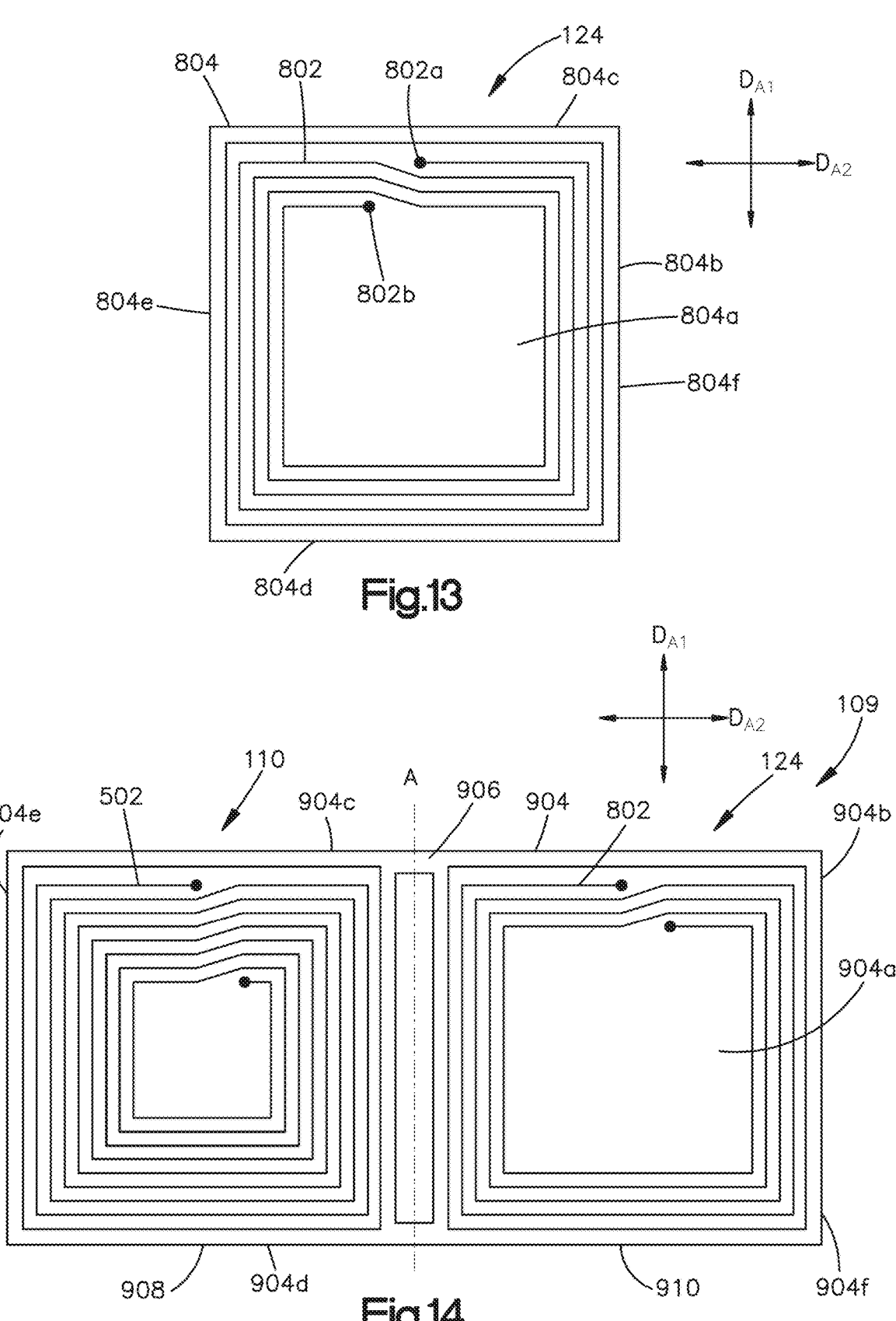
FIG. 13 shows a plan view of the shield of the sensor of FIG. 12 according to one example embodiment.
FIG. 14 shows a plan view of an antenna system according to one example embodiment that can be used to implement the antenna system of the sensor of FIG. 12, where the antenna system includes an antenna coil and a shield coil supported by a common substrate.

As an alternative to ferrite, and with reference to FIGS. 12 and 13, the sensor 100 can comprise a shield 124 disposed between the antenna 110 and the implant 114. The shield 124 can have at least one inductive shield coil 802 and a substrate 804 that supports the shield coil 802. The antenna system 109 of FIG. 2 can comprise the antenna 110 and the shield 124. Further, the shield coil 802 can be connected in series with the at least one antenna coil 502. The shield can be configured to limit magnetic flux passing through the shield 124 or even substantially prevent magnetic flux from passing through the shield 124 altogether. As an electrical current flows in the shield coil 124, the current can mimic the eddy currents in the implant. Consequently, the shield 124 can limit the amount in which the implant 114 beneath the shield 124 is exposed to the magnetic field generated by the antenna 110, or prevent such exposure altogether. In other words, the magnetic field of the shield 124 can cancel a portion of the magnetic field of the antenna 110 that would otherwise extend below the shield 124. Reducing the interaction between the antenna 110 and the implant 114 can result in better performance of the antenna 110 such as a longer wireless communication range between the antenna and the reader 116 and more reliable tuning.

The substrate 804 can be a film or other suitable substrate. In one example, the shield 124 can be implemented as a flexible printed circuit board. The substrate 804 can have a first broadside 804a and a second broadside 804b opposite the first broadside 804a. The substrate 804 can further have a first edge 804c and a second edge 804d opposite one another with respect to a first direction $D_{A1}$. The substrate 804 can yet further have a third edge 804e and a fourth edge 804f opposite one another with respect to the second direction $D_{A2}$, perpendicular to the first direction $D_{A1}$. The first and second broadsides 804a and 804b can extend between the first and second edges 804c and 804d and between the third and fourth edges 804e and 804f The first broadside 804a can be planar along the first and second directions $D_{A1}$ and $D_{A2}$. Similarly, the second broadside 804b can be planar along the first and second directions $D_{A1}$ and $D_{A2}$. The first and second broadsides 804a and 804b can be opposite one another with respect to a third direction $D_{A3}$, perpendicular to both the first and second directions $D_{A1}$ and $D_{A2}$. Note that the directions $D_{A1}$, $D_{A2}$, and $D_{A3}$ can be aligned with the directions $D_1$, $D_2$, and $D_3$ of the at least one sensing element 102 of FIG. 3, or can be angularly offset from the directions $D_1$, $D_2$, and $D_3$.

The substrate 804 can have a height from the first edge 804c to the second edge 804d with respect to the first direction $D_{A1}$. The substrate 804 can further define a width from the third edge 804e to the fourth edge 804f with respect to the second direction $D_{A2}$. The substrate 804 can yet further define a thickness from the first broadside 804a to the second broadside 804b with respect to the third direction $D_{A3}$. The height and width can be greater than the thickness. In some examples, the substrate 804 can have a rectangular shape; however, in alternative examples, the substrate 804 can have any other suitable shape.

The shield coil 802 can be an electrically conductive wire or trace. The shield coil 802 can include a first end 802a and a second end 802b offset from one another. The coil 802 can extend about a center of the coil 802 in a spiral pattern from the first end 802a to the second end 802b such that the second end 802b is spaced closer to the center of the coil 802 than the first end 802a. Thus, the coil 802 can have a plurality of turns. The number of turns can be less than or equal to the total number of turns of the at least one antenna coil 502. The coil 802 can have an overall shape that is substantially square; however, in alternative embodiments, the coil 802 can have another suitable shape.

The antenna 110 and shield 124 can extend along respective planes. When the sensor is assembled, the shield 110 can be disposed below the antenna 124 such that the plane of the antenna 110 is spaced from the plane of the shield 124 along the third direction $D_{A3}$. Thus, the plane of the antenna 110 can face the plane of the shield 124 along the third direction $D_{A3}$. In some embodiments, the respective planes can be substantially parallel to one another, although the respective planes can be offset by another angle such as by less than 30 degrees. One of the broadsides 504a and 504b of the antenna 110 can face one of the broadsides 804a and 804b of the shield 124. Further, the antenna 110 and the shield 124 can define a space between their respective planes with respect to the third direction $D_{A3}$.

In some preferred examples, the shield coil 802 can be configured to carry current in a direction that is opposite that of the antenna coil 502. For example, each of the at least one antenna coil 502 can be wound in a first direction, and the shield coil 802 can be wound in a second direction, opposite from the first direction when the shield coil 802 is disposed below the at least one antenna coil 502. More specifically, the at least one antenna coil 502 can be wound in one of a clockwise and a counterclockwise direction, beginning from an interior of the antenna coil 502, as viewed in a direction towards the implant 114, while the shield coil 802 can be wound in the other one of the clockwise and counterclockwise direction, beginning from an interior of the shield coil 802, as viewed in the direction towards the implant 114. Thus, the shield coil 802 can be configured to generate a magnetic field in a direction that opposes the magnetic field of the at least one antenna coil 502. Further, in some preferred embodiments, the shield coil 802 can have a number of turns that is less than a total number of turns of the at least one antenna coil 502. In some such examples, the shield coil 802 can have approximately half the number of turns of the at least one antenna coil 502. Thus, the shield coil 802 can produce a weaker magnetic field that opposes the magnetic field of the at least one antenna coil 502.

Referring to FIG. 14, in some embodiments, the antenna system 109 can include the antenna coil 502, the shield coil 802, and a substrate 904, where both the antenna coil 502 and shield coil 802 are supported by the substrate 904. Thus, the antenna 110 can include the antenna coil 502 and a first portion 908 of the substrate 904, and the shield 124 can include the shield coil 802 and a second portion 910 of the substrate 904. The antenna system 109 is configured to be bent between an unstacked configuration as shown in FIG. 13 and a stacked configuration (not shown). In the unstacked configuration, the antenna coil 502 and the shield coil 802 are spaced from one another along the second direction $D_{A2}$. Thus, the antenna coil 502 and the shield coils 802 are disposed side-by-side. In the stacked configuration, the substrate 904 is bent about an axis A that extends between the antenna coil 502 and the shield coil 802 along the first direction $D_{A1}$ such that the antenna coil 502 and the shield coil 802 are spaced from one another along the third direction $D_{A3}$, which is perpendicular to both the first and second directions $D_{A1}$ and $D_{A2}$. The antenna coil 502 and shield coil 802 can be wound in the same direction (i.e., clockwise or counterclockwise) when the antenna system 109 is in the unstacked configuration, and can be wound in opposite directions when the antenna system 109 is bent to the stacked configuration.

The substrate 904 can be a film or other suitable substrate. In one example, the assembly can be implemented as a flexible printed circuit board. The substrate 904 can have a first broadside 904a and a second broadside 904b opposite the first broadside 904a. The substrate 904 can further have a first edge 904c and a second edge 904d opposite one another with respect to a first direction $D_{A1}$. The substrate 904 can yet further have a third edge 904e and a fourth edge 904f. The third edge 904e and fourth edge 904f can be spaced opposite one another with respect to the second direction $D_{A2}$ when the substrate 904 is in the unstacked configuration. The first and second broadsides 904a and 904b can extend between the first and second edges 904c and 904d and between the third and fourth edges 904e and 904f. The first broadside 904a can be planar along the first and second directions $D_{A1}$ and $D_{A2}$ when the substrate is in the unstacked configuration. Similarly, the second broadside 904b can be planar along the first and second directions $D_{A1}$ and $D_{A2}$ when the substrate is in the unstacked configuration.

The substrate 904 can have a height from the first edge 904c to the second edge 904d with respect to the first direction $D_{A1}$. The substrate 904 can further define a width from the third edge 904e to the fourth edge 904f with respect to the second direction $D_{A2}$. The substrate 904 can yet further define a thickness from the first broadside 904a to the second broadside 904b with respect to the third direction $D_{A3}$. The height and width can be greater than the thickness. In some examples, the substrate 904 can have a rectangular shape; however, in alternative examples, the substrate 904 can have any other suitable shape.

The antenna 110 and shield 124 can define respective planes. In the unstacked configuration, the respective planes can be substantially in-line with one another. The substrate 904 can include a flexible bend region 906 between the antenna 110 and the shield 124. The substrate 904 can be configured to bend at the bend region 906 so as to transition the antenna system 109 between the unstacked configuration and the stacked configuration. In the stacked configuration, the plane defined by the antenna 110 is spaced from the plane defined by the shield 124 along the third direction $D_{A3}$. Thus, the plane defined by the antenna 110 can face the plane defined by the shield 124 along the third direction $D_{A3}$. For example, the antenna system 109 can be bent such that one of the first and second broadsides 904a and 904b at the first portion 908 of the substrate 904 (e.g., at the antenna coil 502) faces the one of the first and second broadsides 904a and 904b at the second potion 910 of the substrate 904 (e.g., at the shield coil 802).

In the stacked configuration, the plane defined by the antenna 110 can be disposed above the plane defined by the shield 124 with respect to the third direction $D_{A3}$. The respective planes can be substantially parallel to one another, although the respective planes can be offset by another angle such as by less than 30 degrees. Further, the antenna system can define a space between the planes that define the antenna 110 and the shield 124 with respect to the third direction $D_{A3}$ when the antenna system 109 is in the stacked configuration. At least one, up to all, of the electrical components 107 can be disposed in the space between the antenna 110 and the shield 124 as discussed above in relation to FIG. 13.

Figure 15:
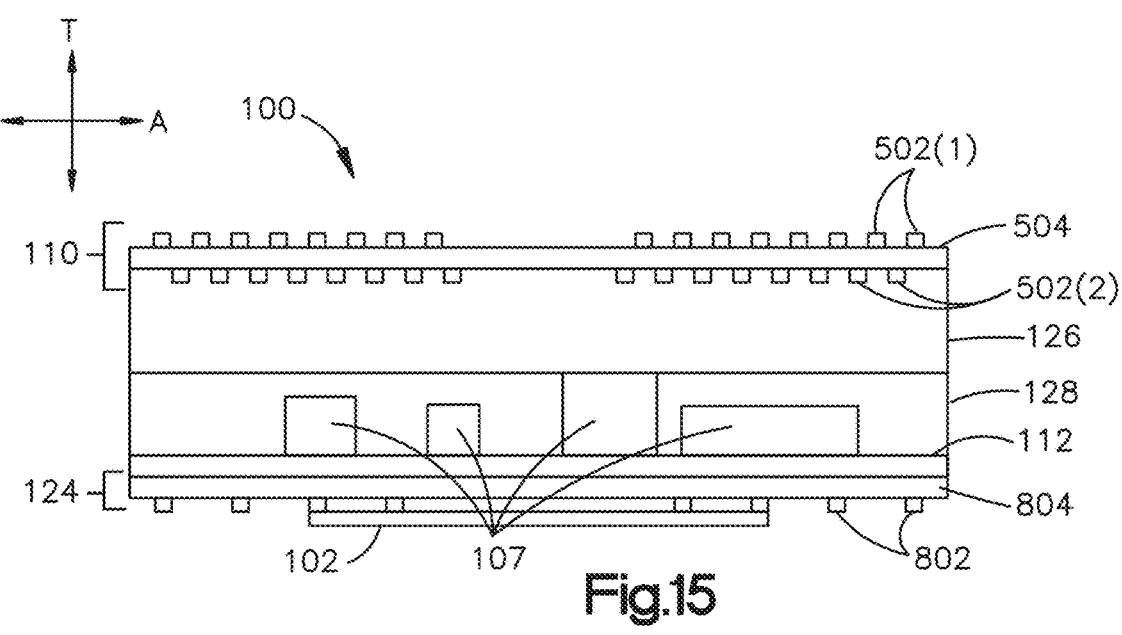
FIG. 15 shows a cross-sectional view of a portion of the sensor system of FIG. 12 according to one example embodiment having electrical components that are disposed between the antenna and the shield.
Figure 16:
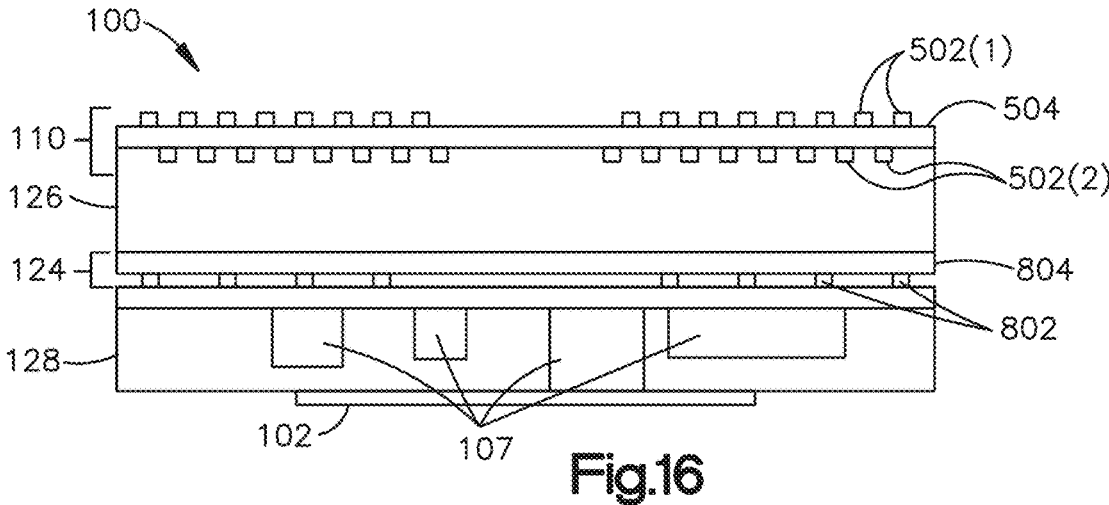
FIG. 16 shows a cross-sectional view of a portion of the sensor system of FIG. 12 according to another example embodiment, where the shield is disposed between the antenna and the electrical components.

Turning now to FIGS. 15 and 16, two exemplary stack-ups of the components of the sensor 100 are shown. In these particular examples, the antenna 110 is illustrated with two antenna coils 502(1) and 502(2), and the coils are shifted relative to one another such that the turns of the antenna coil 502(2) are disposed below the gaps between the turns of the antenna coil 502(1). It will be understood that, in alternative embodiments, the antenna 110 can include only one antenna coil 502(1) or 502(2), or the coils can be aligned, rather than shifted, such that the turns of the antenna coils 502(1) and 502(2) are aligned along the transverse direction T. In a similar manner, the shield 124 can have more than one shield coil disposed over one another or can have only one shield coil.

The shield 124 can be disposed below the antenna 110. For example, the shield 124 can be disposed between the antenna 110 and the implant 114 when the sensor 100 is attached to the implant 114. In at least some embodiments, the shield 124 can be disposed between the antenna 110 and the at least one sensing element 102. In some such embodiments as shown in FIG. 15, the shield 124 can be disposed between the at least one sensing element 102 and at least one of the electrical components 107 such as at least one, up to all of, the measurement device 104, the power device 106, and the wireless communicator 108. Thus, the electrical components 107 can be disposed in the space between the shield 124 and the antenna 110. Note that the components 107 are illustrated schematically in FIGS. 15 and 16, and the particular orientation of the components 107 on the printed circuit board 112 can vary from the orientation shown. Further, the sensor 100 can include various spacers between adjacent layers of the sensor 100, such as spacers 126 and 128. In alternative embodiments as shown in FIG. 16, the electrical components 107 can be disposed below the shield 124. Thus, the shield 124 can be disposed between the antenna 110 and the electrical components 107 such as the measurement device 104, the power device 106, and the wireless communicator 108.

Figure 17:
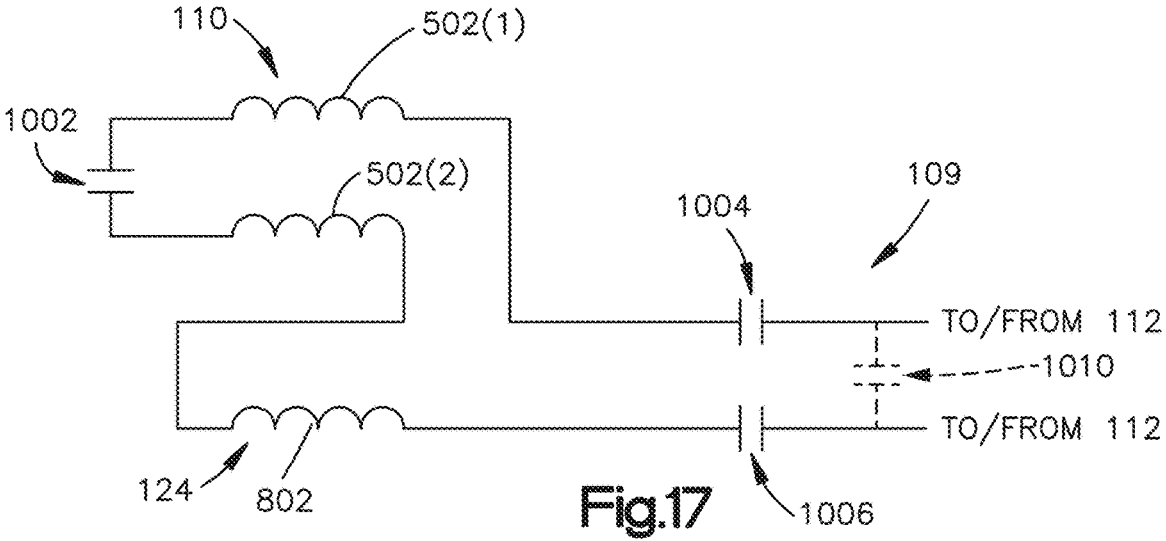
FIG. 17 shows an electrical circuit diagram of the antenna system of FIG. 12 according to one example embodiment, where the antenna system includes the antenna and the shield.

Turning now to FIG. 17, an electrical circuit diagram of one example of the antenna system 109 of FIG. 2 is shown. The antenna system 109 comprises the antenna 110 and the shield 124 connected in series with one another. In this example, the antenna 110 comprises the first inductive antenna coil 502(1) and the second inductive antenna coil 502(2) connected in series with one another, although in alternative embodiments, the antenna 110 can comprise just one inductive antenna coil or more than two inductive coils with capacitors placed between adjacent pairs of the inductive coils. Further, the shield 124 includes one inductive coil 802, although it will be understood that the shield 124 can similarly include more than one inductive coil. The antenna system 109 can comprise at least one, such as a plurality of, capacitors 1002, 1004, 1006. A capacitor 1002 can be connected between the first and second antenna coils 502(1) and 502(2). The capacitor 1002 can cause the self-resonance of the first and second antenna coils 502(1) and 502(2) to be higher, which in turn can decrease losses in the coils 502(1) and 502(2). A capacitor 1004 can be connected in series between the antenna 110 and the electrical components of the sensor 100 such as at least one, up to all of, the measurement device 104, the power device 106, and the wireless communicator 108 of FIG. 2. A capacitor 1006 can be connected in series between the shield 124 and the electrical components of the sensor 100 such as at least one, up to all of, the measurement device 104, the power device 106, and the wireless communicator 108 of FIG. 2. It will be understood that, in alternative embodiments, one or more parallel capacitors can be used. For example, an optional parallel capacitor 1010 can be connected as shown in dashed lines. In some embodiments, the capacitor 1004 can have a capacitance that is equal to a capacitance of the capacitor 1006. The antenna system 109 can be tuned before being implanted onto the metallic implant. The antenna 110 and shield 124 can be tuned together since they are connected in series. After mounting on the sensor 100 onto the metallic implant, the antenna system 109 can maintain its tuning.

Figure 18:
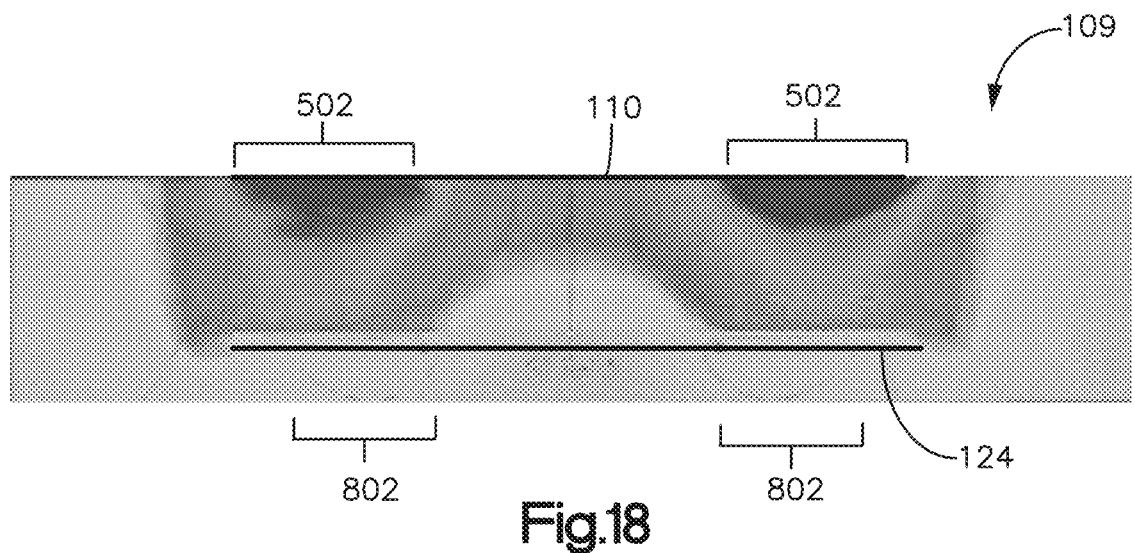
FIG. 18 illustrates the magnetic field of the antenna system of FIG. 12.
Figure 19:
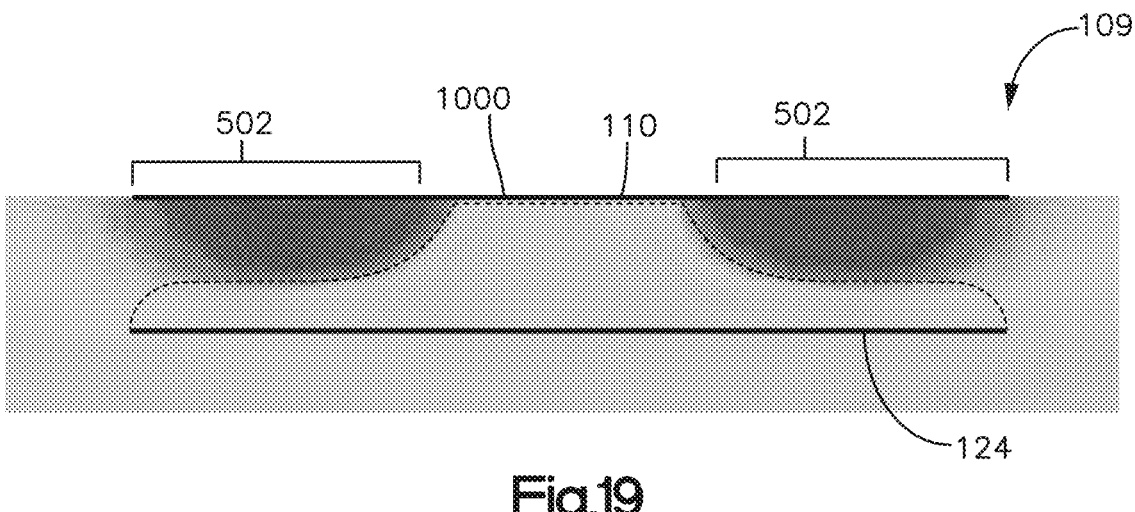
FIG. 19 illustrates the electric field of the antenna system of FIG. 12.

Turning to FIGS. 18 and 19, magnetic and electric fields of the sensor 100 are shown, respectively, where the darker shading indicates areas where the magnetic and electric fields have greater intensity and the lighter shading indicates areas where the magnetic and electric fields have lower intensity. As shown in FIG. 18, the shield 124 generates its own magnetic field when current flows through the shield coil 802. The magnetic field of the shield 124 limits the magnetic flux of the antenna 110 from passing through the shield 124 or prevents the magnetic flux of the antenna 110 from passing through the shield 124 altogether. As shown in FIG. 19, the shield 124 limits the electric field below the shield 124. As a result, the electric field of the antenna 110 does not excite eddy currents, or excites only low magnitude eddy currents, in the implant below the shield 124. Moreover, as shown in FIG. 19, there is a region 1000 defined between the antenna 110 and the shield 124 in which the electric field is relatively low in comparison to the electric field adjacent to the at least one antenna coil 502. The region 1000 is defined in an area that extends from the shield 124 and upwards towards the antenna 110. The region 1000 has a first height directly below the at least one antenna coil 502, and a second height directly below a center of the at least one antenna coil 502 that is greater than the first height. Thus, it can be understood that metallic objects, such as the electrical components 107 and/or the ground plane of the printed circuit board 112, can be positioned in the region 1000 without significantly hurting the performance of the antenna 110.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but it is intended to cover modifications within the spirit and scope of the present disclosure. Further, it should be appreciated, that the term substantially indicates that certain directional components are not absolutely perpendicular to each other and that substantially perpendicular means that the direction has a primary directional component that is perpendicular to another direction.

Embodiments of the disclosure will be understood with reference to the following examples:

EXAMPLE 1

A sensor configured to be implanted into a patient, the sensor comprising:
  at least one sensing element;
  a measurement device in communication with the at least one sensing element, the measurement device including at least one capacitor and configured to measure a discharge time of the at least one capacitor through the at least one sensing element so as to generate a measurement value that is proportional to a value of an anatomical property of the patient observed by the sensor.

EXAMPLE 2

The sensor of example 1, wherein the at least one sensing element comprises a resistor, and the measurement device is configured to measure the discharge time of the at least one capacitor through the resistor so as to generate the measurement value.

EXAMPLE 3

The sensor of any one of the preceding examples, comprising an internal wireless communicator in communication with the measurement device, the wireless communicator configured to wirelessly communicate the measurement value through skin of the patient to an external wireless communicator situated outside of the patient's body.

EXAMPLE 4

The sensor of any one of the preceding examples, wherein the measurement device comprises a time-to-digital converter configured to measure discharge time of the capacitor through the at least one sensing element.

EXAMPLE 5

The sensor of example 4, wherein the measurement device comprises a clock, and the time-to-digital converter is configured to increment in response to a clock signal of the clock.

EXAMPLE 6

The sensor of any of the preceding examples, wherein the sensor comprises a strain gauge that includes the at least one sensing element.

EXAMPLE 7

The sensor of example 6, wherein the strain gauge includes a substrate that carries the at least one sensing element, and the at least one sensing element includes first and second sensing elements, wherein the first and second sensing elements are non-parallel to one another.

EXAMPLE 8

The sensor of example 7, wherein the at least one sensing element includes a third sensing element, wherein the third sensing element is non-parallel to the first and second sensing elements.

EXAMPLE 9

The sensor of example 8, wherein each of the first, second, and third sensing elements includes a longitudinal axis, and the longitudinal axes of the first, second, and third sensing elements intersect one another.

EXAMPLE 10

The sensor of any one of the preceding examples, wherein the at least one sensing element comprises a semiconductor bar-type strain gauge.

EXAMPLE 11

The sensor of example 3, wherein the internal wireless communicator comprises a wireless transmitter, and the sensor comprises an antenna.

EXAMPLE 12

The sensor of example 11, wherein the wireless transmitter is configured to communicate using radio-frequency identification (RFID).

EXAMPLE 13

The sensor of any one of the preceding examples, comprising a power device configured to supply power to the measurement device.

EXAMPLE 14

The sensor of example 13, wherein the power device includes an energy harvesting device.

EXAMPLE 15

The sensor of example 14, wherein the energy harvesting device is configured to capture energy from radio waves communicated to the sensor.

EXAMPLE 16

A system comprising:
  a first sensor configured as recited in any one of the preceding claims; and
  an anatomical implant configured to support the sensor.

EXAMPLE 17

The system of example 16, comprising a second sensor configured as recited in any one of the preceding claims.

EXAMPLE 18

The system of example 17, wherein the first sensor is configured to be supported by the anatomical implant such that the first sensor is aligned with a bone fracture and the second sensor is configured to be supported such that the second sensor is aligned with a portion of healthy bone.

EXAMPLE 19

The system of example 17, wherein the first sensor includes a first unique identifier, and the second sensor includes a second unique identifier, different from the first unique identifier.

EXAMPLE 20

A method of detecting a value of an anatomical property of a patient from at least one sensor implanted into a patient's body, the method comprising steps of:
  charging at least one capacitor of the at least one sensor to a reference voltage; discharging the at least one capacitor through at least one sensing element of the at least one sensor; and
  generating a measurement value that is proportional to the value of the anatomical property, the generating step comprising measuring a discharge time of the at least one capacitor to a trigger voltage.

EXAMPLE 21

The method of example 20, wherein discharging step comprises discharging the at least one capacitor through at least one resistor of the at least one resistive sensing element.

EXAMPLE 22

The method of any one of examples 20 and 21, further comprising wirelessly communicating the measurement value through skin of the patient to an external wireless communicator situated outside of the patient's body.

EXAMPLE 23

The method of any one of examples 20 to 22, wherein the charging step comprises a power device providing power to the at least one capacitor.

EXAMPLE 24

The method of example 23, wherein the charging step comprises capturing energy from a source separate from the at least one sensor at an energy-harvesting device, and providing the energy from the source to the at least one capacitor so as to charge the at least one capacitor.

EXAMPLE 25

The method of example 24, wherein the source is radio waves.

EXAMPLE 26

The method of any one of examples 20 to 25, wherein the generating step comprises measuring the discharge time of the at least one capacitor using a time-to-digital converter.

EXAMPLE 27

The method of any one of examples 20 to 26, wherein the generating step comprises calculating the measurement value based on the discharge time.

EXAMPLE 28

The method of any one of examples 20 to 27, wherein the measurement value is the discharge time.

EXAMPLE 29

The method of any one of examples 20 to 28, wherein the discharging step comprises discharging the at least one capacitor through at least two resistive sensing elements that are non-parallel to one another.

EXAMPLE 30

The method of any one of examples 20 to 29, wherein the discharging step comprises discharging the at least one capacitor through three resistive sensing elements that are non-parallel to one another.

EXAMPLE 31

The method of any one of examples 20 to 30, wherein the wirelessly communicating step comprises communicating the measurement value to the external wireless communicator using radio frequency identification (RFID).

EXAMPLE 32

The method of any one of examples 20 to 31, wherein the wirelessly communicating step comprises communicating a unique identifier to the external wireless communicator that identifies the at least one sensor.

EXAMPLE 33

The method of any one of examples 20 to 32, wherein the measurement value is proportional to strain on the at least one sensor.

EXAMPLE 34

The method of any one of examples 20 to 33, wherein:
  the at least one sensor comprises a first sensor aligned with a bone fracture and a second sensor aligned with healthy bone; and
  the method comprises:
    performing the charging, discharging, generating, and wirelessly communicating steps for the first sensor to generate a first measurement value and for the second sensor to generate a second measurement value; and
    generating a comparison value based on the first and second measurement values.

EXAMPLE 35

A sensor configured to be implanted into a patient, the sensor comprising:
  a semiconductor strain gauge having a substrate and first, second, and third sensing elements arranged on the substrate such that the first, second, and third sensing elements are non-parallel to one another; and a measurement device in communication with the first to third sensing elements, the measurement device configured to generate a measurement value that is proportional to a value of an anatomical property of the patient observed by the sensor.

EXAMPLE 36

The sensor of example 35, comprising an internal wireless communicator in communication with the measurement device, the wireless communicator configured to wirelessly communicate the measurement value through the skin of the patient to an external wireless communicator situated outside of the patient's body.

EXAMPLE 37

The sensor of example 35, wherein the internal wireless communicator comprises a wireless transmitter, and the sensor includes an antenna.

EXAMPLE 38

The sensor of example 37, wherein the sensor comprises a printed circuit board that includes a substrate, and each of the measurement device and the wireless transmitter is implemented as an integrated circuit that is mounted onto the substrate.

EXAMPLE 39

The sensor of example 38, wherein the printed circuit board is disposed between the semiconductor strain gauge and the antenna.

EXAMPLE 40

The sensor of example 35, comprising a cover that configured to be disposed over the semiconductor strain gauge, the measurement device, and the antenna such that the antenna is disposed between the semiconductor strain gauge and the cover.

EXAMPLE 41

The sensor of any one of examples 35 to 40, wherein the measurement device includes at least one capacitor and is configured measure a discharge time of the at least one capacitor through the first to third sensing elements so as to generate the measurement value.

EXAMPLE 42

The sensor of example 41, wherein the measurement device comprises a time-to-digital converter configured to measure the discharge time.

EXAMPLE 43

A system comprising:

an anatomical implant configured to be implanted into a patient;

a first sensor supported by the anatomical implant, and a second sensor, each of the first and second sensors comprising:

at least one sensing element;

a measurement device in communication with the at least one sensing element, the measurement device configured to generate a measurement value that is proportional to a value of an anatomical property of the patient; and an internal wireless communicator configured to wirelessly communicate the measurement value and a unique identifier through skin of the patient to an external wireless communicator situated outside of the patient, wherein the unique identifier of the first sensor is different from the unique identifier of the second sensor.

EXAMPLE 44

The system of example 43, wherein:

the at least one sensing element of each of the first and second sensors comprises a resistor; and the measurement device of each of the first and second sensors comprises a capacitor and is configured to measure a discharge time of the capacitor through a corresponding one of the resistors so as to generate a corresponding one of the measurement values.

EXAMPLE 45

The system of example 44, wherein each of the first and second measurement devices comprises a time-to-digital converter configured to measure the discharge time of a corresponding one of the capacitors through a corresponding at least one sensing element.

EXAMPLE 46

The system of any one of examples 43 to 45, wherein each internal wireless communicator comprises a radio frequency identification (RFID) communicator.

EXAMPLE 47

The system of any one of examples 43 to 46, wherein each of the measurement devices comprises a clock, and the time-to-digital converter of each measurement device is configured to increment in response to a clock signal of a corresponding one of the clocks.

EXAMPLE 48

The system of any of examples 43 to 47, wherein each of the first and second sensors comprises a strain gauge that includes a corresponding at least one sensing element.

EXAMPLE 49

The system of example 48, wherein each strain gauge includes a substrate that carries a corresponding at least one sensing element, and the corresponding at least one sensing element includes first and second sensing elements, wherein the first and second sensing elements are non-parallel to one another.

EXAMPLE 50

The system of example 49, wherein the at least one sensing element includes a third sensing element, wherein the third sensing element is non-parallel to the first and second sensing elements.

EXAMPLE 51

The system of example 50, wherein each of the first, second, and third sensing elements includes a longitudinal axis, and the longitudinal axes of the first, second, and third sensing elements intersect one another.

EXAMPLE 52

The system of any one of examples 43 to 51, wherein each sensing element comprises a semiconductor bar-type strain gauge.

EXAMPLE 53

The system of any one of examples 43 to 52, wherein each internal wireless communicator comprises a wireless transmitter, and the sensor comprises an antenna.

EXAMPLE 54

The system of example 53, wherein each wireless transmitter is configured to communicate using radio-frequency identification (RFID).

EXAMPLE 55

The system of any one of examples 43 to 54, wherein each sensor comprises a power device configured to supply power to the measurement device.

EXAMPLE 56

The system of example 55, wherein each power device includes an energy harvesting device.

EXAMPLE 57

The system of example 56, wherein each energy harvesting device is configured to capture energy from radio waves communicated to the energy harvesting device.

EXAMPLE 58

A sensor configured to be implanted into a patient, the sensor comprising:
  at least one sensing element;
  a measurement device in communication with the at least one sensing element, the measurement device configured to generate a measurement value that is proportional to a value of an anatomical property of the patient observed by the sensor;
  an antenna having at least one inductive antenna coil that is wound in a first direction, the antenna coil configured to wirelessly transmit the measurement value to a reader outside of the patient; and
  a shield disposed below the antenna, the shield having at least one inductive shield coil that is connected in series with the antenna coil and is wound in a second direction, opposite the first direction.

EXAMPLE 59

The sensor of example 58, wherein the shield is configured to limit magnetic flux passing through the shield.

EXAMPLE 60

The sensor of any one of examples 58 and 59, wherein the shield coil has a number of turns that is less than a number of turns of the antenna coil.

EXAMPLE 61

The sensor of anyone of examples 58 to 60, wherein the shield coils has a number of turns that is equal to a number of turns of the at least one inductive antenna coil.

EXAMPLE 62

The sensor of any one of examples 58 to 61, wherein the at least one shield coil is configured to generate a magnetic field in a direction that opposes a magnetic field of the at least one antenna coil.

EXAMPLE 63

The sensor of any one of examples 58 to 62, wherein the shield coil is configured to produce a weaker magnetic field than a magnetic field of the at least one antenna coil.

EXAMPLE 64

The sensor of any one of examples 58 to 63, wherein both the antenna and shield are supported by a common substrate.

EXAMPLE 65

The sensor of example 64, wherein the antenna includes the antenna coil and a first portion of the substrate, and the shield includes the shield coil and a second portion of the substrate.

EXAMPLE 66

The sensor of any one of examples 64 and 65, wherein the antenna system is configured to be bent between an unstacked configuration and a stacked configuration, wherein in the unstacked configuration the antenna coil and shield coil are disposed side-by-side, and in the stacked configuration the substrate is bent about an axis that extends between the antenna coil and the shield coil such that the antenna coil is disposed over the shield coil.

EXAMPLE 67

The sensor of example 66, wherein the antenna coil and the shield coil are wound in the same direction when the antenna system is in the unstacked configuration, and are wound in opposite directions when the antenna system is bent to the stacked configuration.

EXAMPLE 68

The sensor of any one of examples 58 to 67, wherein the sensor defines a space between the antenna and the shield.

EXAMPLE 69

The sensor of example 68, wherein the measurement device is disposed in the space between the antenna and the shield.

EXAMPLE 70

The sensor of any one of examples 58 to 69, wherein the antenna comprises two antenna coils supported on opposite sides of a substrate.

EXAMPLE 71

The sensor of example 70, wherein the two antenna coils are connected in series.

EXAMPLE 72

The sensor of example 71, comprising a capacitor connected between the two antenna coils.

EXAMPLE 73

The sensor of any one of examples 70 to 72, wherein the two antenna coils are shifted relative to one another such that turns of a first of the antenna coils are disposed below gaps between turns of a second of the antenna coils.

EXAMPLE 74

The sensor of any one of examples 58 to 73, wherein the shield is disposed between the antenna and the at least one sensing element.

EXAMPLE 75

The sensor of example 74, wherein the shield is disposed between the at least one sensing element and the measurement device.

EXAMPLE 76

The sensor of example 74, wherein the shield is disposed between the antenna and the measurement device.

What is claimed is:

1. A bone plate configured to be implanted into a patient comprising:
   a body having a first side configured to face a portion of a bone of the patient, and a second side that is opposite the first side in a select direction, the body including a first hole and a second hole that each extend from the first side to the second side, the first hole adapted to receive a first bone fastener and the second hole adapted to receive a second bone fastener, and the body defining a recess that extends from the second side toward the first side, wherein the recess is disposed between the first hole and the second hole; and
   a sensor disposed in the recess between the first hole and the second hole, the sensor comprising:
   at least one sensing element having a first side configured to face a portion of a bone of the patient, and a second side that is opposite the first side along the select direction;
   an internal wireless communicator configured to receive a measurement value that is proportional to an anatomical property observed by the sensing element, wherein the internal wireless communicator is disposed outwardly from the at least one sensing element in the select direction;
   an antenna configured to receive the measurement value from the internal wireless communicator, the antenna having at least one inductive antenna coil wound in a first direction about a respective central axis that is configured to wirelessly transmit the measurement value through skin of the patient to an antenna of an external wireless reader outside of the patient; and
   a shield disposed entirely between the sensing element and the antenna with respect to the select direction, the shield having an inductive shield coil that is wound in a second direction, opposite the first direction, about a respective central axis, wherein the shield is configured to limit or substantially prevent magnetic flux from passing through the shield.

2. The bone plate of claim 1, wherein the at least one sensing element comprises a resistor, and the sensor further comprises a measurement device in communication with the at least one sensing element, and the measurement device is configured to generate the measurement value.

3. The bone plate of claim 2, wherein the measurement device comprises at least one capacitor that is configured to measure a discharge time of the at least one capacitor through the resistor so as to generate the measurement value, and the measurement device further comprises a time-to-digital converter configured to measure discharge time of the capacitor through the at least one sensing element.

4. The bone plate of claim 2, comprising a power device configured to supply power to the measurement device, wherein the power device includes an energy harvesting device configured to capture energy from radio waves communicated to the sensor.

5. The bone plate of claim 2, comprising a cover that is configured to cover the recess, the internal wireless communicator, and the at least one sensor such that the measurement device and internal wireless communicator are disposed beneath the cover in the recess.

6. The bone plate of claim 2, wherein the measurement device and internal wireless communicator are stacked over the at least one sensing element.

7. The bone plate of claim 1, wherein the sensor comprises a strain gauge that includes the at least one sensing element, and the anatomical property is strain.

8. The bone plate of claim 7, wherein the strain gauge includes a substrate that carries the at least one sensing element, and the at least one sensing element includes at least first and second sensing elements, wherein the first and second sensing elements are non-parallel to one another.

9. The bone plate of claim 1, wherein the internal wireless communicator comprises a radio-frequency identification (RFID) transponder.

10. The bone plate of claim 1, wherein the sensor is a first sensor, and the bone plate further comprises a second sensor including:
   at least one second sensing element; and
   a second internal wireless communicator configured to receive a second measurement value that is proportional to a second anatomical property observed by the at least one second sensing element; and
   a second antenna having at least one second inductive antenna coil configured to wirelessly transmit the second measurement value through skin of the patient,
   wherein the first sensor is configured to be associated with a bone fracture, the second sensor is configured to be associated with healthy bone, and the measurement value of the first sensor is compared to the second measurement value to gauge bone healing at the bone fracture.

11. A sensor configured to be implanted into a patient, the sensor comprising:

a semiconductor strain gauge having a substrate and first, second, and third sensing elements carried by the substrate and each configured to detect one or both of torsional and bending forces, each sensing element having a respective first end and a respective second end that is offset from the first end along a respective central axis, and each sensing element comprising a respective resistor that is linear bar that extends between the respective first and second ends along the respective central axis, z wherein the first, second, and third sensing elements are disposed at an outer surface of the substrate, and the central axes of the first, second, and third sensing elements are non-parallel to one another;

a measurement device in communication with the first to third sensing elements, the measurement device configured to generate a measurement value that is proportional to a value of an anatomical property of the patient observed by the sensor;

an internal wireless communicator in communication with the measurement device, the wireless communicator configured to receive the measurement value;

an antenna in communication with the internal wireless communicator and offset from the sensing elements along a select direction, the antenna having at least one antenna coil wound in a first winding direction about a respective central axis, the antenna coil configured to wirelessly transmit the measurement value through skin of the patient to an external wireless reader outside of the patient; and a shield having at least one inductive shield coil that is connected in series with the antenna and is wound in a second winding direction, opposite the first winding direction, about a respective central axis, wherein the shield is disposed entirely between the antenna and the at least one sensing element with respect to the select direction, wherein the substrate is a flexible printed circuit board having a first edge and a second edge spaced from the first edge along a first linear direction and the first end of each of the first, second, and third sensing elements are positioned between the first edge and the second end of each of the first, second, and third sensing elements with respect to the first linear direction, and wherein the substrate includes a third edge and a fourth edge spaced from the third edge along a second linear direction perpendicular to the first linear direction and a straight line extending from the third edge to the fourth edge passes through each of the first, second, and third sensing elements.

12. The sensor of claim 11, wherein the measurement device includes at least one capacitor, and the measurement device is configured to measure the discharge time of the at least one capacitor through each respective resistor so as to generate the measurement value.

13. The sensor of claim 12, wherein the measurement device comprises a time-to-digital converter configured to measure the discharge time through each resistor.

14. The system of claim 11, wherein each sensing element comprises a semiconductor bar-type strain gauge.

15. A sensor configured to be implanted into a patient, the sensor comprising:

at least one sensing element;

a measurement device in communication with the at least one sensing element, the measurement device configured to generate a measurement value that is proportional to a value of an anatomical property of the patient observed by the sensor;

an antenna having at least one inductive antenna coil that is wound in a first direction about a respective central-axis, the at least one antenna coil configured to wirelessly transmit the measurement value to a reader outside of the patient; and a shield having at least one inductive shield coil that is connected in series with the antenna coils and is wound in a second direction, opposite the first direction, about a respective central axis that is parallel to the respective central axis of the antenna, wherein the shield is configured to limit or substantially prevent magnetic flux from passing through the shield, wherein the shield is disposed entirely between the antenna and the at least one sensing element with respect to a direction along which the antenna and the at least one sensing element are separated from each other.

16. The sensor of claim 15, wherein the at least one shield coil is configured to generate a magnetic field in a direction that opposes a magnetic field of the at least one antenna coil.

17. The sensor of claim 15, wherein the shield is disposed between the at least one sensing element and the measurement device.

18. The sensor of claim 15, wherein the shield is disposed between the antenna and the measurement device.

19. The sensor of claim 15, wherein the first and second antenna coils are wound in a first plane, the inductive shield coil is wound in a second plane, and the first and second planes are spaced from one another along the third direction.

* * * * *